(12) United States Patent
Hancock et al.

(10) Patent No.: US 6,337,317 B1
(45) Date of Patent: Jan. 8, 2002

(54) ANTIMICROBIAL PEPTIDES AND METHODS OF USE THEREOF

(75) Inventors: Robert E. W. Hancock, Vancouver; Lijuan Zhang, Richmond, both of (CA)

(73) Assignee: The University of British Columbia, Vancouver (CA)

( * ) Notice: Subject to any disclaimer, the term of this patent is extended or adjusted under 35 U.S.C. 154(b) by 0 days.

(21) Appl. No.: 09/604,864

(22) Filed: Jun. 27, 2000

(51) Int. Cl.[7] .................. A61K 38/10; C07K 7/08
(52) U.S. Cl. .................. 514/13; 514/13; 514/12; 530/324; 530/326; 530/300; 435/69.1
(58) Field of Search .................. 514/13, 12; 530/324, 530/326; 435/69.1

(56) References Cited

U.S. PATENT DOCUMENTS

| | | |
|---|---|---|
| 5,593,866 A | 1/1997 | Hancock et al. |
| 5,688,767 A | 11/1997 | Hancock et al. |
| 5,707,855 A | 1/1998 | Hancock et al. |
| 5,789,377 A | 8/1998 | Hancock et al. |
| 5,877,274 A | 3/1999 | Hancock et al. |
| 6,040,435 A | 3/2000 | Hancock et al. |
| 6,057,291 A | 5/2000 | Hancock et al. |
| 6,172,185 B1 | 1/2001 | Hancock et al. |
| 6,191,254 B1 | 2/2001 | Falla et al. |

FOREIGN PATENT DOCUMENTS

WO   WO-9803192 A1 * 1/1998

OTHER PUBLICATIONS

Fahrner, R. L. et al. Solution Structure of Protegrin–1, a Broad–spectrum Antimicrobial Peptide from Porcine Leukocytes. Chemistry and Biology (Jul. 1996) vol. 3 (7) 543–550.*

* cited by examiner

*Primary Examiner*—Christopher S. F. Low
*Assistant Examiner*—Chih-Min Kam
(74) *Attorney, Agent, or Firm*—Gary Cary Ware & Freidenrich LLP; Lisa A. Haile

(57) ABSTRACT

A class of cationic, polyphemusin-like peptides having antimicrobial activity is provided. Examples of such peptides include FRWCFRVCYKGRCRYKCR (SEQ ID NO:3), RRWCFRVCYKGFCRYKCR (SEQ ID NO:4), and RRWCFRVCYRGRFCYRKCR (SEQ ID NO:11). Also provided are methods for inhibiting the growth of microbes such as bacteria, yeast and viruses utilizing the peptides of the invention. The peptides are particularly useful for inhibiting endotoxemia in a subject.

5 Claims, 7 Drawing Sheets

Tachyplesin I    KWCFRVCYRG ICYRRCR-CONH$_2$
Polyphemusin I  RRWCFRVCYRG FCYRKCR-CONH$_2$
PV5             RRWCFRVCYRG<u>R</u>FCYRKCR-CONH$_2$
PV7             RRWCFRVCY<u>K</u>G FC<u>RY</u>KCR-CONH$_2$
PV8             <u>F</u>RWCFRVCY<u>K</u>G <u>R</u>C<u>RY</u>KCR-CONH$_2$

FIGURE 1

FIG. 2A
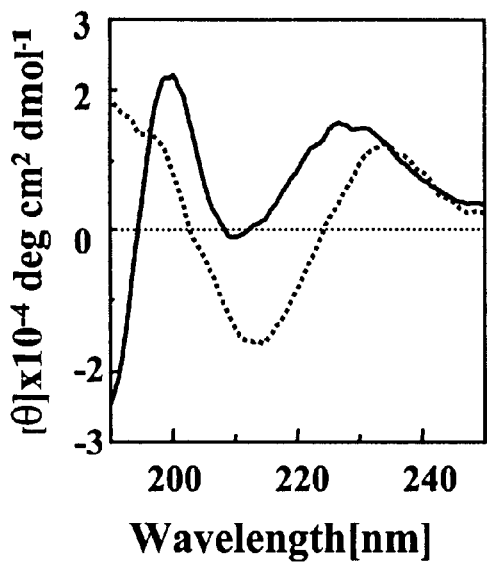
FIG. 2B
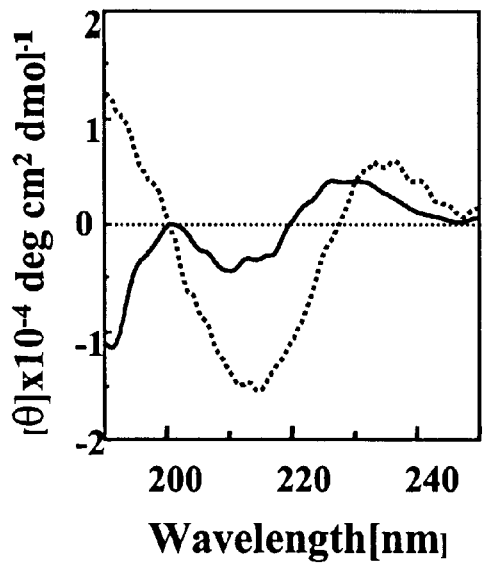
FIG. 2C
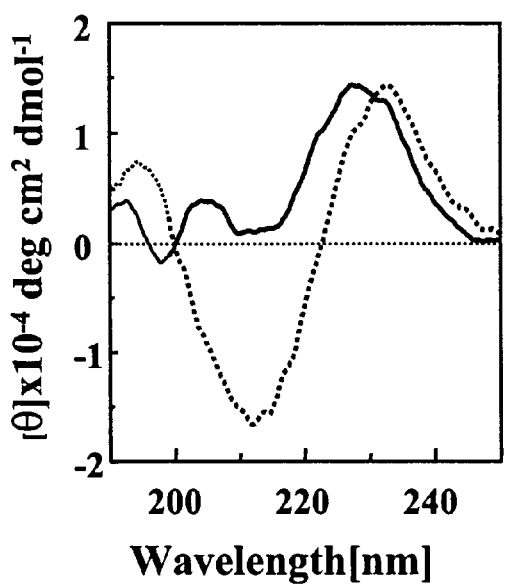
FIG. 2D
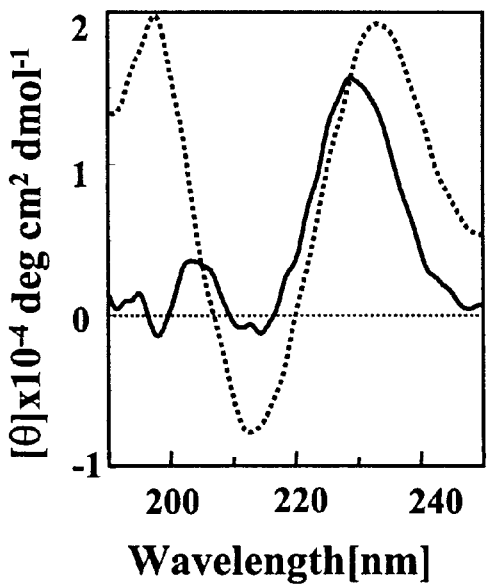
Figure 2

SEQUENCE LISTING

<160> NUMBER OF SEQ ID NOS: 19

<210> SEQ ID NO 1
<211> LENGTH: 17
<212> TYPE: PRT
<213> ORGANISM: Limulus polyphemus

<400> SEQUENCE: 1

Trp Cys Phe Ala Val Cys Arg Arg Gly Arg Cys Arg Tyr Lys Cys Arg
 1               5                  10                  15

Arg

<210> SEQ ID NO 2
<211> LENGTH: 17
<212> TYPE: PRT
<213> ORGANISM: Limulus polyphemus

<400> SEQUENCE: 2

Trp Cys Phe Ala Val Cys Tyr Arg Gly Arg Cys Arg Arg Lys Cys Arg
 1               5                  10                  15

Arg

<210> SEQ ID NO 3
<211> LENGTH: 18
<212> TYPE: PRT
<213> ORGANISM: Limulus polyphemus

<400> SEQUENCE: 3

Phe Arg Trp Cys Phe Arg Val Cys Tyr Lys Gly Arg Cys Arg Tyr Lys
 1               5                  10                  15

Cys Arg

<210> SEQ ID NO 4
<211> LENGTH: 18
<212> TYPE: PRT
<213> ORGANISM: Limulus polyphemus

<400> SEQUENCE: 4

Arg Arg Trp Cys Phe Arg Val Cys Tyr Lys Gly Phe Cys Arg Tyr Lys
 1               5                  10                  15

Cys Arg

<210> SEQ ID NO 5
<211> LENGTH: 18
<212> TYPE: PRT
<213> ORGANISM: Limulus polyphemus

<400> SEQUENCE: 5

Arg Arg Trp Cys Phe Arg Val Cys Tyr Arg Gly Phe Cys Arg Tyr Phe
 1               5                  10                  15

Cys Arg

<210> SEQ ID NO 6
<211> LENGTH: 18
<212> TYPE: PRT
<213> ORGANISM: Limulus polyphemus

```
<400> SEQUENCE: 6

Arg Arg Trp Cys Phe Ile Val Cys Arg Arg Gly Ala Cys Tyr Arg Arg
 1               5                  10                  15

Cys Arg

<210> SEQ ID NO 7
<211> LENGTH: 19
<212> TYPE: PRT
<213> ORGANISM: Limulus polyphemus

<400> SEQUENCE: 7

Arg Arg Trp Cys Phe Ile Val Cys Arg Arg Gly Arg Cys Tyr Val Ala
 1               5                  10                  15

Cys Arg Arg

<210> SEQ ID NO 8
<211> LENGTH: 18
<212> TYPE: PRT
<213> ORGANISM: Limulus polyphemus

<400> SEQUENCE: 8

Arg Val Trp Cys Arg Arg Cys Tyr Arg Gly Phe Cys Arg Tyr Phe
 1               5                  10                  15

Cys Arg

<210> SEQ ID NO 9
<211> LENGTH: 18
<212> TYPE: PRT
<213> ORGANISM: Limulus polyphemus

<400> SEQUENCE: 9

Arg Val Trp Cys Arg Tyr Arg Cys Tyr Arg Gly Phe Cys Arg Arg Phe
 1               5                  10                  15

Cys Arg

<210> SEQ ID NO 10
<211> LENGTH: 18
<212> TYPE: PRT
<213> ORGANISM: Limulus polyphemus

<400> SEQUENCE: 10

Arg Arg Trp Cys Arg Arg Val Cys Tyr Ala Gly Phe Cys Tyr Arg Lys
 1               5                  10                  15

Cys Arg

<210> SEQ ID NO 11
<211> LENGTH: 19
<212> TYPE: PRT
<213> ORGANISM: Limulus polyphemus

<400> SEQUENCE: 11

Arg Arg Trp Cys Phe Arg Val Cys Tyr Arg Gly Arg Phe Cys Tyr Arg
 1               5                  10                  15

Lys Cys Arg

<210> SEQ ID NO 12
<211> LENGTH: 17
<212> TYPE: PRT
<213> ORGANISM: Tachypleus tridentatus
```

```
<400> SEQUENCE: 12

Lys Trp Cys Phe Arg Val Cys Tyr Arg Gly Ile Cys Tyr Arg Arg Cys
 1               5                  10                  15
Arg

<210> SEQ ID NO 13
<211> LENGTH: 18
<212> TYPE: PRT
<213> ORGANISM: Limulus polyphemus

<400> SEQUENCE: 13

Arg Arg Trp Cys Phe Arg Val Cys Tyr Arg Gly Phe Cys Tyr Arg Lys
 1               5                  10                  15
Cys Arg

<210> SEQ ID NO 14
<211> LENGTH: 17
<212> TYPE: PRT
<213> ORGANISM: Artificial Sequence
<220> FEATURE:
<223> OTHER INFORMATION: cationic antimicrobial peptide
<221> NAME/KEY: VARIANT
<222> LOCATION: 4
<223> OTHER INFORMATION: Xaa = Ala, Val, Ile, Leu, Tyr, Phe or Trp
<221> NAME/KEY: VARIANT
<222> LOCATION: 7, 13
<223> OTHER INFORMATION: Xaa = Lys, Arg, His, Phe, Tyr or Trp
<221> NAME/KEY: VARIANT
<222> LOCATION: 10
<223> OTHER INFORMATION: Xaa = Lys, Arg or His

<400> SEQUENCE: 14

Trp Cys Phe Xaa Val Cys Xaa Arg Gly Xaa Cys Arg Xaa Lys Cys Arg
 1               5                  10                  15
Arg

<210> SEQ ID NO 15
<211> LENGTH: 18
<212> TYPE: PRT
<213> ORGANISM: Artificial Sequence
<220> FEATURE:
<223> OTHER INFORMATION: cationic antimicrobial peptide
<221> NAME/KEY: VARIANT
<222> LOCATION: 1, 12, 16
<223> OTHER INFORMATION: Xaa = Lys, Arg, His, Phe, Tyr or Trp
<221> NAME/KEY: VARIANT
<222> LOCATION: 10, 14
<223> OTHER INFORMATION: Xaa = Lys, Arg or His
<221> NAME/KEY: VARIANT
<222> LOCATION: 15
<223> OTHER INFORMATION: Xaa = Ala, Val, Ile, Leu, Tyr, Phe or Trp

<400> SEQUENCE: 15

Xaa Arg Trp Cys Phe Arg Val Cys Tyr Xaa Gly Xaa Cys Xaa Xaa Xaa
 1               5                  10                  15
Cys Arg

<210> SEQ ID NO 16
<211> LENGTH: 19
<212> TYPE: PRT
<213> ORGANISM: Artificial Sequence
<220> FEATURE:
<223> OTHER INFORMATION: cationic antimicrobial peptide
<221> NAME/KEY: VARIANT
<222> LOCATION: 6
<223> OTHER INFORMATION: Xaa = Ala, Val, Ile, Leu, Tyr, Phe or Trp
<221> NAME/KEY: VARIANT
```

```
<222> LOCATION: 9
<223> OTHER INFORMATION: Xaa = Lys, Arg or His
<221> NAME/KEY: VARIANT
<222> LOCATION: 12, 15, 16
<223> OTHER INFORMATION: Xaa = Arg, Val or Ala
<221> NAME/KEY: VARIANT
<222> LOCATION: 19
<223> OTHER INFORMATION: Xaa = Lys, Arg, His or is absent

<400> SEQUENCE: 16

Arg Arg Trp Cys Phe Xaa Val Cys Xaa Arg Gly Xaa Cys Tyr Xaa Xaa
 1               5                  10                  15

Cys Arg Xaa

<210> SEQ ID NO 17
<211> LENGTH: 18
<212> TYPE: PRT
<213> ORGANISM: Artificial Sequence
<220> FEATURE:
<223> OTHER INFORMATION: cationic antimicrobial peptide
<221> NAME/KEY: VARIANT
<222> LOCATION: 2, 16
<223> OTHER INFORMATION: Xaa = Ala, Val, Ile, Leu, Tyr, Phe or Trp
<221> NAME/KEY: VARIANT
<222> LOCATION: 5, 7, 14
<223> OTHER INFORMATION: Xaa = Lys, Arg or His
<221> NAME/KEY: VARIANT
<222> LOCATION: 6, 15
<223> OTHER INFORMATION: Xaa = Lys, Arg, His, Phe, Tyr or Trp

<400> SEQUENCE: 17

Arg Xaa Trp Cys Xaa Xaa Xaa Cys Tyr Arg Gly Phe Cys Xaa Xaa Xaa
 1               5                  10                  15

Cys Arg

<210> SEQ ID NO 18
<211> LENGTH: 18
<212> TYPE: PRT
<213> ORGANISM: Artificial Sequence
<220> FEATURE:
<223> OTHER INFORMATION: cationic antimicrobial peptide
<221> NAME/KEY: VARIANT
<222> LOCATION: 5
<223> OTHER INFORMATION: Xaa = Lys, Arg or His
<221> NAME/KEY: VARIANT
<222> LOCATION: 10
<223> OTHER INFORMATION: Xaa = Ala, Val, Ile, Leu, Tyr, Phe or Trp

<400> SEQUENCE: 18

Arg Arg Trp Cys Xaa Arg Val Cys Tyr Xaa Gly Phe Cys Tyr Arg Lys
 1               5                  10                  15

Cys Arg

<210> SEQ ID NO 19
<211> LENGTH: 19
<212> TYPE: PRT
<213> ORGANISM: Artificial Sequence
<220> FEATURE:
<223> OTHER INFORMATION: cationic antimicrobial peptide
<221> NAME/KEY: VARIANT
<222> LOCATION: 12
<223> OTHER INFORMATION: Xaa = Lys, Arg, or His

<400> SEQUENCE: 19

Arg Arg Trp Cys Phe Arg Val Cys Tyr Arg Gly Xaa Phe Cys Tyr Arg
 1               5                  10                  15

Lys Cys Arg
```

ANTIMICROBIAL PEPTIDES AND METHODS OF USE THEREOF

FIELD OF THE INVENTION

This invention relates generally to antimicrobial peptides and specifically to a new class of antimicrobial peptides referred to as polyphemusin-like peptides.

BACKGROUND OF THE INVENTION

In 1981, the self-promoted uptake hypothesis was first proposed to explain the mechanism of action of polycationic antibiotics in *Pseudomonas aeruginosa*. According to this hypothesis, polycations interact with sites on the outer membranes of Gram-negative bacteria at which divalent cations cross-bridge adjacent lipopolysaccharide molecules. Due to their higher affinity for these sites, polycations displace the divalent cations and, since the polycations are bulkier than the divalent cations, cause structural perturbations in the outer membrane. These perturbations result in increased outer membrane permeability to compounds such as the β-lactam antibiotic nitrocefin, the eukaryotic non-specific defense protein lysozyme and to hydrophobic substances. By analogy, molecules accessing this pathway are proposed to promote their own uptake.

It has been clearly demonstrated that the outer membranes of Gram-negative bacteria are semipermeable molecular "sieves" which restrict access of antibiotics and host defense molecules to their targets within the bacterial cell. Thus, cations and polycations which access the self-promoted uptake system are, by virtue of their ability to interact with and break down the outer membrane permeability barrier, capable of increasing the susceptibility of Gram-negative pathogenic bacteria to antibiotics and host defense molecules. Hancock and Wong demonstrated that a broad range of such compounds could overcome the permeability barrier and coined the name "permeabilizers" to describe them (Hancock and Wong, *Antimicrob. Agents Chemother.*, 26:48, 1984). While self-promoted uptake and permeabilizers were first described for *P. aeruginosa*, they have now been described for a variety of Gram-negative bacteria.

Over the past decade, non-specific defense molecules have been described in many animals, including insects and humans. One subset of these molecules have in common the following features: (a) they are small peptides, usually 15–35 amino acid residues in length, (b) they contain four or more positively charged amino acid residues, either lysines or arginines, and (c) they are found in high abundance in the organisms from which they derive. Several of these molecules have been isolated, amino acid sequenced and described in the patent literature (e.g., cecropins: W08900199, WO 8805826, WO8604356, WO 8805826; defensins: EP 193351, EP 85250, EP 162161, U.S. Pat. No. 4,659,692, WO 8911291). However, only limited amounts of these peptides can be isolated from the host species. For example, Sawyer et al. (*Infect. Immun.* 56:693, 1988) isolated 100–200 mg of rabbit neutrophil defensins 1 and 2 from $10^9$ primed peritoneal neutrophils or lipopolysaccharide-elicited alveolar macrophages (i.e., the numbers present in a whole animal).

Production of these peptides using peptide synthesis technology produces peptides in limited amounts and is expensive when scaled up or when many variant peptides must be produced. Also, structural analysis is difficult without specific incorporation of $^{15}$N- and $^{13}$C-tagged amino acids which is prohibitively expensive using amino acid synthesis technology.

The hemocytes of the horseshoe crab contain a unique family of β-sheet peptide antibiotics, including polyphemusins I and II and tachyplesins I to III (Nakamura et al. (1988) *J. Biol. Chem.* 263:16709–16713; and Miyata et al. (1989) *J. Biochem.* 106:663–668). These peptides are structurally closely-related and are highly abundant in the hemocyte debris. Polyphemusins, isolated from *Limulus polyphemus*, and tachyplesins, isolated from *Tachypleus tridentatus, Tachypleus gigas* and *Carcinoscorpius rotundicauda*, are 18 and 17 amino acid residues in length, respectively. These peptides exhibit a variety of biological activities such as inhibition of the growth of bacteria and fungi and inhibition of the replication of enveloped viruses including vesicular stomatitis virus, influenza A virus and human immunodeficiency virus (HIV)-1 (Miyata et al. (1989) *J. Biochem.* 106:663–668; Masuda et al. (1992) *Biochem. Biophys. Res. Commun.* 189:845–850; Morimoto et al. (1991) *Chemotherapy* 37:206–211; and Murakami et al. (1991) *Chemotherapy* 37:327–334), herpes virus, hepatitis B and C viruses, and the like. Other studies indicated that tachyplesin I binds to anionic molecules such as DNA and lipopolysaccharides (LPS), and inhibits the LPS-mediated activation of factor I, which is an initiation factor in the Limulus clotting cascade (Nakamura et al., supra; Miyata et al., supra; Yonezawa et al, (1992) *Biochemistry* 31:2998–3004). Therefore, these arthropod peptides are of special pharmaceutical interest as potential therapeutic agents for anti-endotoxin therapy.

Among the five arthropod peptides, only the secondary structure of tachyplesin I has been determined by nuclear magnetic resonance spectroscopy (Kawano et aL (1990) *J. Biol. Chem.* 265:15365–15367). It was found to have a fairly rigid planar conformation consisting of an anti-parallel β-sheet structure, constrained by two disulphide bridges and connected by a type II β-turn. In this planar confirmation, five bulky hydrophobic side groups are located on one side of the plane and six cationic side groups are distributed at the "tail" of the molecule. Like many naturally occurring antimicrobial peptides, polyphemusins and tachyplesins are polycationic and amphipathic, and the C-terminus is amidated. These properties have been implicated in the mode of action and toxicity of tachyplesin I (Park et al. (1992) *Biochemistry* 31:12241–12247). Numerous studies of the anti-viral action of this group of peptides against HIV-1 have been carried out (Tamamura et al. (1993) *Biochim. Biophys. Acta* 1163:209–216, Tamamura et aL (1998) *Bioorg. Med. Chem.* 6:1033–1041; Arakaki et al. (1999) *J. Virol.* 73:1719–1723). However few studies have focused on the antimicrobial mechanism and anti-endotoxin activity. Limited data has indicated that, at high concentrations (>100 fold the inhibitory concentration), tachyplesin I causes morphological and permeability changes of bacterial cells and human erythrocytes, and increases the $K^+$ permeability of *S. aureus* and *E. coli* cells, concomitantly reducing cell viability (Katsu et al. (1993) *Bio. Pharm. Bull.* 16:178–181).

Gram-negative bacteria have two cell envelope membranes. The outer membrane is an asymmetric membrane with the bulky glycolipid lipopolysaccharide (LPS) covering more than 90% of the cell surface in its outer leaflet, and phospholipids with a composition similar to that of the cytoplasmic membrane in its inner leaflet. Many antimicrobial cationic peptides have been shown to interact with the LPS of the Gram-negative bacterial outer membrane and pass across this membrane by self-promoted uptake, followed by interaction with and insertion into the negatively charged cytoplasmic membrane (Hancock (1997) *Lancet* 349:418–422). However, the target of these cationic peptides is not well understood. Although for many peptides the formation of lesions has been observed in model membranes, there has been little convincing evidence to link such interactions to the event(s) causing bacterial cell death, and it has been proposed that at least some peptides cross the cytoplasmic membrane to access cytoplasmic targets like polyanionic nucleic acids (Kagan et al. (1990) Proc. Natl. Acad. Sci. U.S.A. 87:210–214; Ludtke et al. (1996) Biochemistry 35:13723–13728).

There is thus a need to develop polypeptides having a broad range of potent antimicrobial activity against a plurality of microorganisms, including gram negative bacteria, gram positive bacteria, fungi, protozoa, viruses and the like.

SUMMARY OF THE INVENTION

The present invention provides cationic peptides, referred to as polyphemusin-like peptides, which have antimicrobial activity. Also included are analogs, derivatives and conservative variations thereof.

In a first embodiment, the invention provides an isolated peptide having an amino acid sequence selected from the group consisting of: $WCFZ_5VCZ_2RGZ_3CRZ_2KCRR$, $Z_2RWCFRVCYZ_3GZ_2CZ_3Z_5Z_2CR$, $RRWCFZ_5VCZ_3RGZ_4CYZ_4Z_4CRZ_1$, $RZ_5WCZ_3Z_2Z_3CYRGFCZ_3Z_2Z_5CR$, $RRWCZ_3RVCYZ_5GFCYRKCR$, and $RRWCFRVCYRGZ_3FCYRKCR$; wherein $Z_1$ is a basic amino acid residue or no amino acid residue; $Z_2$ is a basic or aromatic residue, $Z_3$ is a basic amino acid residue, $Z_4$ is arginine, valine or alanine, and $Z_5$ is an aromatic or aliphatic amino acid residue. Exemplary peptides of these general formulae include SEQ ID NO:1 to SEQ ID NO:11.

The invention also provides a method of inhibiting the growth of microbes such as bacteria and yeast, comprising contacting the bacteria or yeast with an inhibiting effective amount of a peptide having an amino acid sequence selected from the group consisting of $WCFZ_5VCZ_2RGZ_3CRZ_2KCRR$, $Z_2RWCFRVCYZ_3GZ_2CZ_3Z_5Z_2CR$, $RRWCFZ_5VCZ_3RGZ_4CYZ_4Z_4CRZ_1$, $RZ_5WCZ_3Z_2Z_3CYRGFCZ_3Z_2Z_5CR$, $RRWCZ_3RVCYZ_5GFCYRKCR$, and $RRWCFRVCYRGZ_3FCYRKCR$; wherein $Z_1$ is a basic amino acid residue or no amino acid residue; $Z_2$ is a basic or aromatic residue, $Z_3$ is a basic amino acid residue, $Z_4$ is arginine, valine or alanine, and $Z_5$ is an aromatic or aliphatic amino acid residue, alone, or in combination with an antibiotic. Exemplary peptides used in the practice of invention method are peptides having the amino acid sequences set forth in SEQ ID NO:1 to SEQ ID NO:11. Peptides of the invention can be administered in combination with antibiotics, lysosymes, anti-TNF (tumor necrosis factor) antibodies and TNF antagonists. Classes of antibiotics which can be used for synergistic therapy with the peptides of the invention include aminoglycoside, penicillin, cephalosporine, fluoroquinolone, carbepenem, tetracycline and macrolide.

In another embodiment, the invention provides a method of inhibiting an endotoxemia or sepsis associated disorder in a subject having or at risk of having such a disorder, comprising administering to the subject a therapeutically effective amount of a peptide of the invention.

BRIEF DESCRIPTION OF THE DRAWINGS

FIG. 1 shows the amino acid sequence (using the single letter amino acid code) of tachyplesin, polyphemusin I and its variants. Disulfide linkages are shown by solid lines. The amino acids substituted in variants are underlined (PV5: SEQ ID NO:11; PV7: SEQ ID NO:4; and PV8: SEQ ID NO:3).

FIGS. 2A through 2D show a circular dichlroism spectra of Polyphemusin I and selected invention peptides. FIG. 2A shows a spectrum of polyphemusin I; FIG. 2B shows a spectrum of SEQ ID NO:11 (PV5); FIG. 2C shows a spectrum of SEQ ID NO:4 (PV7); and FIG. 2D shows a spectrum of SEQ ID NO:3 (PV8). The spectra are shown in phosphate buffer (solid lines) and in 10 mM SDS (dotted lines). Peptides were used at a concentration of 25 µM.

FIG. 5A is a plot of the surface pressure increase as a function of peptide concentration. Monolayers were spread with mixed lipids (POPC:egg-PG:CL in a ratio of 78:4.7:14.7, v/v), creating an initial pressure of 20±1 mN/m and allowed to stabilize for 5 min before peptide addition. Titration of the surface pressure increase was accomplished by adding successive amounts of peptide to the subphase while continuously monitoring the surface pressure of the film. FIG. 5B shows the influence on surface pressure of the addition of 1 µg/ml peptides to the aqueous subphase bathing monolayers made from either POPC, POPE, egg-PG or CL. The results shown are the averages of two independent experiments.

DETAILED DESCRIPTION OF THE INVENTION

Figure 3:
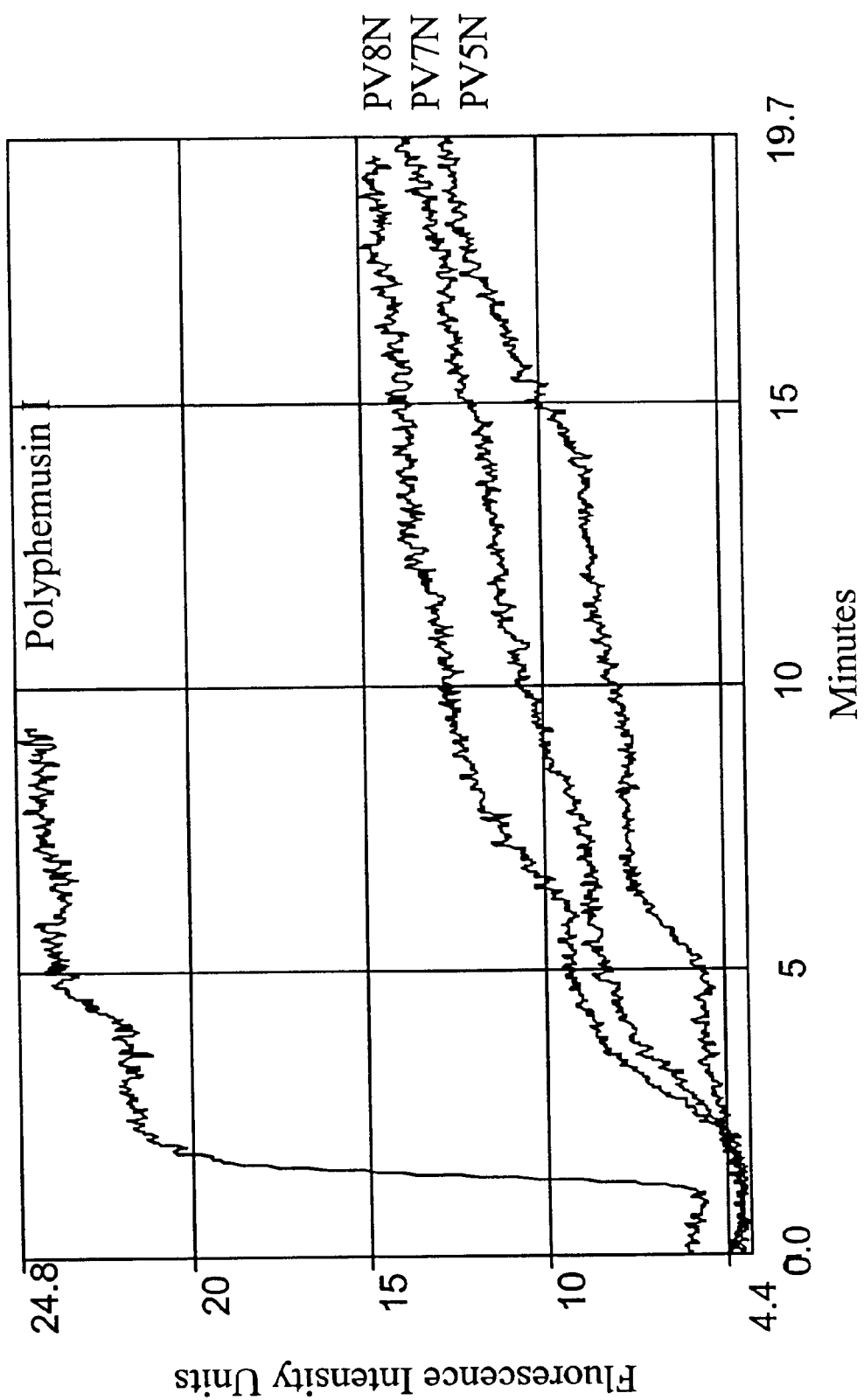
FIG. 3 shows E. coli DC2 cytoplasmic membrane depolarization by peptides as assessed by the $diSC_35$ assay. The arrowhead indicates the time at which 0.25 µg/ml peptide was added. PV5: SEQ ID NO:11; PV7: SEQ ID NO:4; and PV8: SEQ ID NO:3.

The present invention provides cationic peptides which have antimicrobial activity and are highly active at inhibiting the growth of antibiotic-resistant organisms. These peptides are useful for inhibiting microbial infection or growth, as well reducing the effects of endotoxemia and are often synergistic with conventional antibiotics and/or lysozyme. In addition, such peptides are useful as antifungal agents, antitumor agents, or antiviral agents.

The term "antimicrobial" as used herein means that the peptides of the present invention inhibit, prevent, or destroy the growth or proliferation of microbes such as bacteria, fungi, viruses or the like. The term "antiviral" as used herein means that the peptides of the present invention inhibit, prevent or destroy the growth or proliferation of viruses or of virally-infected cells. The term "anti-tumor" as used herein means that the peptides of the present invention may be used to inhibit the growth of or destroy tumors. The term "antifungal" as used herein means that the peptides of the present invention may be used to inhibit the growth of, or destroy fungi.

In a first embodiment, the invention provides an isolated antimicrobial peptide having an amino acid sequence: WCFZ$_5$VCZ$_2$RGZ$_3$CRZ$_2$KCRR, (SEQ ID NO: 14) Z$_2$RWCFRVCYZ$_3$GZ$_2$CZ$_3$Z$_5$Z$_2$CR,(SEQ ID NO:15) RRWCFZ$_5$VCZ$_3$RGZ$_4$CYZ$_4$Z$_4$CRZ$_1$,(SEQ ID NO:16) RZ$_5$WCZ$_3$Z$_2$Z$_3$CYRGFCZ$_3$Z$_2$Z$_5$CR,(SEQ ID NO:17) RRWCZ$_3$RVCYZ$_5$GFCYRKCR,(SEQ ID NO:18) and RRWCFRVCYRGZ$_3$FCYRKCR;(SEQ ID NO:19) wherein $Z_1$ is a basic amino acid residue or no amino acid residue; $Z_2$ is a basic or aromatic residue, $Z_3$ is a basic amino acid residue, $Z_4$ is arginine, valine or alanine, and $Z_5$ is an aromatic or aliphatic amino acid residue.

In the protein sequences presented,(SEQ ID NO:1 to SEQ ID NO:11), the variable $Z_1$ represents an amino acid having a basic side chain or the absence of an amino acid residue at that position in the polypeptide sequence. Exemplary "basic" amino acids include lysine, arginine, histidine, and the like. The variable $Z_2$ represents an amino acid having a basic side chain or an aromatic side chain. Exemplary amino acids of this class include lysine, arginine, histidine, phenylalanine, tryptophan, tyrosine, and the like. The variable $Z_3$ represents an amino acid having a basic side chain. The variable $Z_4$ represents the amino acids arginine, valine or alanine. The variable $Z_5$ represents an amino acid having an aromatic side chain or an aliphatic side chain. Exemplary amino acids of this class include phenylalanine, tyrosine, tryptophan, alanine, valine, leucine, isoleucine, glycine, and the like.

Examples of such peptides of the invention include but are not limited to: WCFAVCRRGRCRYKCRR (SEQ ID NO:1), WCFAVCYRGRCRRKCRR (SEQ ID NO:2), FRWCFRVCYKGRCRYKCR (SEQ ID NO:3), RRWCFRVCYKGFCRYKCR (SEQ ID NO:4), RRWCFRVCYRGFCRYFCR (SEQ ID NO:5), RRWCFIVCRRGACYRRCR (SEQ ID NO:6), RRWCFIVCRRGRCYVACRR (SEQ ID NO:7), RVWCRRRCYRGFCRYFCR (SEQ ID NO:8), RVWCRYRCYRGFCRRFCR (SEQ ID NO:9), RRWCRRVCYAGFCYRKCR (SEQ ID NO:10), and RRWCFRVCYRGRFCYRKCR (SEQ ID NO:11) analogs, derivatives and conservative variations thereof, wherein the peptides have antimicrobial activity. The peptides of the invention include SEQ ID NO:1 to SEQ ID NO:11, as well as the broader groups of peptides having hydrophilic and hydrophobic substitutions, and conservative variations thereof.

Invention peptides include polyphemusin-like peptides depicted in SEQ ID NO:1 to SEQ ID NO:11, as well as analogues or derivatives thereof, as long as the bioactivity of the peptide remains. Minor modifications of the primary amino acid sequence of the peptides of the invention may result in peptides which have substantially equivalent activity as compared to the specific peptides described herein. Such modifications may be deliberate, as by site-directed mutagenesis, or may be spontaneous. All of the peptides produced by these modifications are included herein as long as the biological activity of the original peptide still exists. All peptide sequences presented herein are shown with the amino-terminal amino acid residue in the first (left-most position) and the carboxy-terminal amino acid residue in the last (right-most position).

Further, deletion of one or more amino acids can also result in a modification of the structure of the resultant molecule without significantly altering its biological activity. This can lead to the development of a smaller active molecule which would also have utility. For example, amino or carboxy terminal amino acids which may not be required for biological activity of the particular peptide can be removed. Peptides of the invention include any analog, homolog, mutant, isomer or derivative of the peptides disclosed in the present invention, so long as the bioactivity as described herein is remains. All peptides were synthesized using L amino acids, however, all D forms of the peptides can be synthetically produced. In addition, carboxy-terminal derivatives can be produced, such as carboxy-terminal methyl esters, carboxy-terminal amides, and the like, in order to increase the antimicrobial activity of a peptide of the invention. One of skill in the art could perform a Mimimal Inhibitory Concentration (MIC) assay, for example, as described herein, to identify other related peptides, analogs, or derivatives of invention peptides.

Invention peptides can readily be modified at the carboxy terminal by methods known to those of skill in the art. Modifications of the carboxy terminus include amidation, and the like.

The peptides of the invention include peptides which are conservative variations of those peptides specifically exemplified herein. The term "conservative variation" as used herein denotes the replacement of an amino acid residue by another, biologically similar residue. Examples of conservative variations include the substitution of one hydrophobic residue such as isoleucine, valine, leucine, alanine, cysteine, glycine, phenylalanine, proline, tryptophan, tyrosine, norleucine or methionine for another, or the substitution of one polar residue for another, such as the substitution of arginine for lysine and vice versa, of glutamic acid for aspartic acid, and vice versa, glutamine for asparagine, and vice versa, and the like. Neutral hydrophilic amino acids which can be substituted for one another include asparagine, glutamine, serine and threonine. The term "conservative variation" also includes the use of a substituted amino acid in place of an unsubstituted parent amino acid provided that the biologic activity of the peptide is maintained. Such conservative substitutions are within the definition of the classes of the peptides of the invention with respect to $Z_1$, $Z_2$, $Z_3$, $Z_4$, and $Z_5$.

Polyphemusin and structural variants of polyphemusin described herein are beta-hairpin loop-containing peptides. Each peptide contains two anti-parallel beta strands which are stabilized by two disulphide bonds, and in the loop region, between the beta strand regions, there is a beta turn. Amino acid residues located at the amino and carboxyl termini and which are outside the beta strand regions form the tail region of a peptide.

The amino acid sequences of polyphemusin I and structural analogs of polyphemusin I are shown in FIG. 1. Preferred structural variations are designed to increase amphipathicity. Among the three illustrative variants synthesized, the closest structural analog to polyphemusin I is SEQ ID NO:4 (PV7), in which there is a positional switch between R14 and Y15, as well as a conservative substitution at position 10 (R10 to K10). SEQ ID NO:11(PV5) is a variant with an additional arginine residue inserted between G11 and F12 in the loop region. This structural modification increases the total positive charge of the peptide and also increases the size of the loop. In SEQ ID NO:3 (PV8), the residues at positions 1 and 12 are switched (F12 to R12 and R1 to F1) resulting in an increase in the net positive charge and hydrophilicity of the loop. The switch also alters the tail region by decreasing flexibility and increasing hydrophobicity, due to the bulky aromatic ring and hydropathic nature of phenylalanine. In general, all three of these variants were predicted to have increased amphipathicity compared to polyphemusin I as judged from molecular modeling using the InsightII protein-peptide modeling program (Molecular Simulations, Inc., San Diego, Calif.). In addition, the variants have altered loop regions that are predicted to be more hydrophilic and for one variant peptide, (SEQ ID NO:11), larger.

The biological activity of the peptides can be determined by standard methods known to those of skill in the art, such as a "minimal inhibitory concentration" (MIC) assay (see Wu and Hancock (1999) *J. Biol Chem.* 274:29–35 and Examples section). A MIC assay allows the determination of the lowest concentration of peptide that inhibits the multiplication and growth of mircoorganisms. Changes in the microorganism population are assessed by measuring the optical density (OD) of the population in broth or medium. Peptide MIC's can be determined for a variety of micoorganisms under a variety of conditions. Another assay for the biological activity of the peptides is a "fractional inhibitory concentration" (FIC) assay. This assay is especially useful for determining synergistic effects between the peptides of the invention, and between invention peptides and other compounds such as known antibiotics. A FIC assay employs the strategy of a MIC assay with additional variable(s), e.g., known antibiotics. One type of FIC assay is performed in a microwell plate containing microorganisms in broth. Peptides, in a range of dilutions, is added to each well following a patter of one dimension of the microwell plate, and antibiotics, in the other dimension. The FIC is calculated by looking at the impact of an antibiotic on the MIC of the peptide and the reciprocal relationship. An FIC of one indicates that the influence of the compounds is additive and an FIC of less than one indicates synergy. Preferably, an FIC of less than 0.5 is obtained for synergism. As used herein, FIC can be determined as follows:

$$FIC = \frac{MIC(\text{peptide in combination}) + MIC(\text{antibiotic in combination})}{MIC(\text{peptide alone}) \; MIC(\text{antibiotic alone})}$$

Bacterial endotoxin (LPS) is highly toxic and can cause high mortality in both humans and animals when released during Gram-negative bacterial infection. Galactosamine-treated mice exposed to moderate does of endotoxin typically die from endotoxic shock within 17 hours following exposure. Invention peptides can be tested for their ability to protect mice against endotoxin-induced death (see Examples section). The anti-endotoxic activity of invention peptides also can be tested in an in vitro assay using a macrophage cell line (Gough et al. (1996) *Infect. Immun.* 64:4922–4927; and Examples section).

The toxicity of invention peptides can be assessed using a hemolytic assay in which the ability of the peptides to lyse human red blood cells is assessed (Zhang et al. (1999) *Biochemistry* 38:8102–8111; and Examples section).

The biological activity of invention peptides can also be assessed by examining the ability of the peptides to interact with bacterial membranes and membrane components (liposomes) and by their ability to permeabilize bacterial membranes. (see Examples section).

Peptides of the invention can be synthesized by such commonly used methods as t-BOC or FMOC protection of alpha-amino groups. Both methods involve stepwise syntheses whereby a single amino acid is added at each step starting from the carboxyll-terminus of the peptide (See, Coligan et al., *Current Protocols in Immunology,* Wiley Interscience, 1991, Unit 9). Peptides of the invention can also be synthesized by the solid phase peptide synthesis methods well known in the art. (Merrifield, *J. Am. Chem. Soc.,* 85:2149, 1962), and Stewart and Young, *Solid Phase Peptides Synthesis,* Pierce, Rockford, Ill. (1984)). Peptides can be synthesized using a copoly(styrene-divinylbenzene) containing 0.1–1.0 mMol amines/g polymer. On completion of chemical synthesis, the peptides can be deprotected and cleaved from the polymer by treatment with liquid HF-10% anisole for about 0.25 to 1 hour at 0° C. After evaporation of the reagents, the peptides are extracted from the polymer with 1% acetic acid solution which is then lyophilized to yield the crude material. This can typically be purified by such techniques as gel filtration on Sephadex G-15 using 5% acetic acid as a solvent, by high pressure liquid chromatography, and the like. Lyophilization of appropriate fractions of the column will yield the homogeneous peptide or peptide derivatives, which can then be characterized by such standard techniques as amino acid analysis, thin layer chromatography, high performance liquid chromatography, ultraviolet absorption spectroscopy, molar rotation, solubility, and assessed by the solid phase Edman degradation (see e.g Protein Purification, M. P. Deutscher, ed. Methods in Enzymology, Vol 182, Academic Press, 1990). Automated synthesis using FMOC solid phase synthetic methods can be achieved using an automated peptide synthesizer (Model 432A, Applied Biosystems, Inc.). Peptides are oxidized in Trix-DMSO-isopropanol at pH 7.5 for about 15 to about 20 hours at about 23° C. to permit the formation of disulphide bonds (Tam et al. (1991) *J. Am. Chem. Soc* 113:6657–6662). Following disulphide bond formation, the suspension is purified using reverse phase FPLC by which a yield of about 20% can be obtained.

Invention polypeptides can also be synthesized using a fusion protein microbial method in which an anionic carrier peptide is fused to a cationic peptide. A method for such microbial production of cationic peptides having antimicrobial activity is provided in U.S. Pat. No. 5,593,866, issued Jan. 14, 1997, the entire contents of which are incorporated by reference herein.

The invention includes isolated polynucleotides encoding: WCFZ$_5$VCZ$_2$RGZ$_3$CRZ$_2$KCRR,(SEQ ID NO:14) Z$_2$RWCFRVCYZ$_3$GZ$_2$CZ$_3$Z$_5$Z$_2$CR,(SEQ ID NO:15) RRWCFZ$_5$VCZ$_3$RGZ$_4$CYZ$_4$Z$_4$CRZ$_1$,(SEQ ID NO:16) RZ$_5$WCZ$_3$Z$_2$Z$_3$CYRGFCZ$_3$Z$_2$Z$_5$CR,(SEQ ID NO:17) RRWCZ$_3$RVCYZ$_5$GFCYRKCR,(SEQ ID NO:18) and RRWCFRVCYRGZ$_3$FCYRKCR;(SEQ ID NO:19) wherein Z$_1$ is a basic amino acid residue or no amino acid residue; Z$_2$ is a basic or aromatic residue, Z$_3$ is a basic amino acid residue, Z$_4$ is arginine, valine or alanine, and Z$_5$ is an aromatic or aliphatic amino acid residue.

More specifically, the invention also includes isolated polynucleotides encoding: WCFAVCRRGRCRYKCRR (SEQ ID NO:1), WCFAVCYRGRCRRKCRR (SEQ ID NO:2), FRWCFRVCYKGRCRYKCR (SEQ ID NO:3), RRWCFRVCYKGFCRYKCR (SEQ ID NO:4), RRWCFRVCYRGFCRYFCR (SEQ ID NO:5), RRWCFIVCRRGACYRRCR (SEQ ID NO:6), RRWCFIVCRRGRCYVACRR (SEQ ID NO:7), RVWCRRRCYRGFCRYFCR (SEQ ID NO:8), RVWCRYRCYRGFCRRFCR (SEQ ID NO:9), RRWCRRVCYAGFCYRKCR (SEQ ID NO:10), and RRWCFRVCYRGRFCYRKCR (SEQ ID NO:11).

In addition, the invention includes isolated polynucleotides which encode analogs, mutants and variants of the peptides of the invention. The term "isolated" as used herein refers to a polynucleotide substantially free of proteins, lipids, nucleic acids, for example, with which it is naturally associated. As used herein, "polynucleotide" refers to a polymer of deoxyribonucleotides or ribonucleotides, in the form of a separate fragment or as a component of a larger construct. DNA encoding a peptide of the invention can be assembled from cDNA fragments or from oligonucleotides which provide a synthetic gene which is capable of being expressed in a recombinant transcriptional unit. Polynucleotide sequences of the invention include DNA, RNA and cDNA sequences. A polynucleotide sequence can be deduced from the genetic code, however, the degeneracy of the code must be taken into account. Polynucleotides of the invention include sequences which are degenerate as a result of the genetic code. Such polynucleotides are useful for the recombinant production of large quantities of a peptide of interest, such as the peptides of SEQ ID NO:1 to SEQ NO ID:11.

In the present invention, the polynucleotides encoding the cationic peptides of the invention may be inserted into a recombinant "expression vector". The term "expression vector" refers to a plasmid, virus or other vehicle known in the art that has been manipulated by insertion or incorporation of cationic genetic sequences. Such expression vectors of the invention are preferably plasmids which contain a promoter sequence which facilitates the efficient transcription of the inserted genetic sequence in the host. The expression vector typically contains an origin of replication, a promoter, as well as specific genes which allow phenotypic selection of the transformed cells. For example, the expression of the peptides of the invention can be placed under control of $E.$ $coli$ chromosomal DNA comprising a lactose or lac operon which mediates lactose utilization by elaborating the enzyme beta-galactosidase. The lac control system can be induced by IPTG. A plasmid can be constructed to contain the lac Iq repressor gene, permitting repression of the lac promoter until IPTG is added. Other promoter systems known in the art include beta lactamase, lambda promoters, the protein A promoter, and the tryptophan promoter systems. While these are the most commonly used, other microbial promoters, both inducible and constitutive, can be utilized as well. The vector contains a replicon site and control sequences which are derived from species compatible with the host cell. In addition, the vector may carry specific gene(s) which are capable of providing phenotypic selection in transformed cells. For example, the beta-lactamase gene confers ampicillin resistance to those transformed cells containing the vector with the beta-lactamase gene.

Transformation of a host cell with the polynucleotide may be carried out by conventional techniques well known to those skilled in the art. For example, where the host is prokaryotic, such as $E.$ $coli$, competent cells which are capable of DNA uptake can be prepared from cells harvested after exponential growth and subsequently treated by the $CaCl_2$ method using procedures well known in the art. Alternatively, $MgCl_2$ or RbCl could be used.

In addition to conventional chemical methods of transformation, the plasmid vectors of the invention may be introduced into a host cell by physical means, such as by electroporation or microinjection. Electroporation allows transfer of the vector by high voltage electric impulse, which creates pores in the plasma membrane of the host and is performed according to methods well known in the art. Additionally, cloned DNA can be introduced into host cells by protoplast fusion, using methods well known in the art.

DNA sequences encoding the cationic peptides can be expressed in vivo by DNA transfer into a suitable host cell. "Host cells" of the invention are those in which a vector can be propagated and its DNA expressed. The term also includes any progeny of the subject host cell. It is understood that not all progeny are identical to the parental cell, since there may be mutations that occur during replication. However, such progeny are included when the terms above are used. Preferred host cells of the invention include $E.$ $coli$, $S.$ $aureus$ and $P.$ $aeruginosa$, although other Gram-negative and Gram-positive organisms known in the art can be utilized as long as the expression vectors contain an origin of replication to permit expression in the host.

The cationic peptide polynucleotide sequence used according to the method of the invention can be isolated from an organism or synthesized in the laboratory. Specific DNA sequences encoding the cationic peptide of interest can be obtained by: 1) isolation of a double-stranded DNA sequence from the genomic DNA; 2) chemical manufacture of a DNA sequence to provide the necessary codons for the cationic peptide of interest; and 3) in vitro synthesis of a double-stranded DNA sequence by reverse transcription of mRNA isolated from a donor cell. In the latter case, a double-stranded DNA complement of mRNA is eventually formed which is generally referred to as cDNA.

The synthesis of DNA sequences is frequently the method of choice when the entire sequence of amino acid residues of the desired peptide product is known. In the present invention, the synthesis of a DNA sequence has the advantage of allowing the incorporation of codons which are more likely to be recognized by a bacterial host, thereby permitting high level expression without difficulties in translation. In addition, virtually any peptide can be synthesized, including those encoding natural cationic peptides, variants of the same, or synthetic peptides.

When the entire sequence of the desired peptide is not known, the direct synthesis of DNA sequences is not possible and the method of choice is the formation of cDNA sequences. Among the standard procedures for isolating cDNA sequences of interest is the formation of plasmid or phage containing cDNA libraries which are derived from reverse transcription of mRNA which is abundant in donor cells that have a high level of genetic expression. When used in combination with polymerase chain reaction technology, even rare expression products can be cloned. In those cases where significant portions of the amino acid sequence of the cationic peptide are known, the production of labeled single or double-stranded DNA or RNA probe sequences duplicating a sequence putatively present in the target cDNA may be employed in DNA/DNA hybridization procedures which are carried out on cloned copies of the cDNA which have been denatured into a single stranded form (Jay et al. (1983) $Nuc.$ $Acid$ $Res,$ 11:2325).

The invention also provides a method of inhibiting the growth of bacteria comprising contacting the bacteria with an inhibiting effective amount of a peptide of the invention, including WCFZ$_5$VCZ$_2$RGZ$_3$CRZ$_2$KCRR,(SEQ ID NO:14) Z$_2$RWCFRVCYZ$_3$GZ$_2$CZ$_3$Z$_5$Z$_2$CR,(SEQ ID NO:15) RRWCFZ$_5$VCZ$_3$RGZ$_4$CYZ$_4$Z$_4$CRZ$_1$,(SEQ ID NO:16) RZ$_5$WCZ$_3$Z$_2$Z$_3$CYRGFCZ$_3$Z$_2$Z$_5$CR,(SEQ ID NO:17) RRWCZ$_3$RVCYZ$_5$GFCYRKCR,(SEQ ID NO:18) and RRWCFRVCYRGZ$_3$FCYRKCR;(SEQ ID NO:19) wherein $Z_1$ is a basic amino acid residue or no amino acid residue; $Z_2$ is a basic or aromatic residue, $Z_3$ is a basic amino acid residue, $Z_4$ is arginine, valine or alanine, and $Z_5$ is an aromatic or aliphatic amino acid residue.

More specifically, the invention provides a method of inhibiting the growth of bacteria comprising contacting the bacteria with an inhibiting effective amount of a peptide of the invention, such as WCFAVCRRGRCRYKCRR (SEQ ID NO:1), WCFAVCYRGRCRRKCRR (SEQ ID NO:2), FRWCFRVCYKGRCRYKCR (SEQ ID NO:3), RRWCFRVCYKGFCRYKCR (SEQ ID NO:4), RRWCFRVCYRGFCRYFCR (SEQ ID NO:5), RRWCFIVCRRGACYRRCR (SEQ ID NO:6), RRWCFIVCRRGRCYVACRR (SEQ ID NO:7), RVWCRRRCYRGFCRYFCR (SEQ ID NO:8), RVWCRYRCYRGFCRRFCR (SEQ ID NO:9), RRWCRRVCYAGFCYRKCR (SEQ ID NO:10), and RRWCFRVCYRGRFCYRKCR (SEQ ID NO:11) and analogs, derivatives, or conservative variations thereof.

The term "contacting" refers to exposing the bacteria to the peptide so that the peptide can effectively inhibit, kill, or lyse bacteria, bind endotoxin (LPS), or permeabilize gram-negative bacterial outer membranes. Contacting may be in vitro, for example by adding the peptide to a bacterial culture to test for susceptibility of the bacteria to the peptide. Contacting may be in vivo, for example, administering the peptide to a subject with a bacterial disorder, such as septic shock. "Ihhibiting" or "inhibiting effective amount" refers to the amount of peptide which is required to cause a bacteriostatic or bactericidal effect. Examples of bacteria which may be inhibited include *E. cloacae, Staphylococcus epidermidis, Enterococcus facaelis* and *Staphylococcus aureus, Escherichia coli, Pseduomonas aeurginosa,* and *Salmonella typhimurium*.

The method of inhibiting the growth of bacteria may further include the addition of antibiotics for combination or synergistic therapy. The appropriate antibiotic administered will typically depend on the susceptibility of the bacteria such as whether the bacteria is gram negative or gram positive, and will be easily discemable by one of skill in the art. Examples of particular classes of antibiotics useful for synergistic therapy with the peptides of the invention include aminoglycosides (e.g., tobramycin), penicillins (e.g., piperacillin), cephalosporins (e.g., ceftazidime), fluoroquinolones (e.g., ciprofloxacin), carbepenems (e.g., imipenem), tetracyclines and macrolides (e.g., erythromycin and clarithromycin). The method of inhibiting the growth of bacteria may further include the addition of antibiotics for combination or synergistic therapy. The appropriate antibiotic administered will typically depend on the susceptibility of the bacteria such as whether the bacteria is gram negative or gram positive, and will be easily discemable by one of skill in the art. Further to the antibiotics listed above, typical antibiotics include amino-glycosides (amikacin, gentamicin, kanamycin, netilmicin, tobramycin, streptomycin, azithromycin, clarithromycin, erythromycin, erythromycin estolate/ethylsuccinate/gluceptate/lactobionate/stearate), beta-lactams such as penicillins (e.g., penicillin G, penicillin V, methicillin, nafcillin, oxacillin, cloxacillin, dicloxacillin, ampicillin, amoxicillin, ticarcillin, carbenicillin, mezlocillin, azlocillin and piperacillin), or cephalosporins (e.g., cephalothin, cefazolin, cefaclor, cefamandole, cefoxitin, cefuroxime, cefonicid, cefinetazole, cefotetan, cefprozil, loracarbef, cefetamet, cefoperazone, cefotaxime, ceftizoxime, ceftriaxone, ceftazidime, cefepime, cefixime, cefpodoxime, and cefsulodin). Other classes of antibiotics include carbapenems (e.g., imipenem), monobactams (e.g., aztreonam), quinolones (e.g., fleroxacin, nalidixic acid, norfloxacin, ciprofloxacin, ofloxacin, enoxacin, lomefloxacin and cinoxacin), tetracyclines (e.g., doxycycline, minocycline, tetracycline), and glycopeptides (e.g., vancomycin, teicoplanin), for example. Other antibiotics include chloramphenicol, clindamycin, trimethoprim, sulfamethoxazole, nitrofurantoin, rifampin and mupirocin.

The peptides and/or analogues or derivatives thereof may be administered to any host, including a human or non-human animal, in an amount effective to inhibit not only growth of a bacterium, but also a virus or fungus (yeast). These peptides are useful as antimicrobial agents, antiviral agents, and antifungal agents. The peptides and/or analogues or derivatives thereof may be administered to any host, including a human or non-human animal, in an amount effective to inhibit not only growth of a bacterium, but also a virus or fungus. These peptides are useful as antimicrobial agents, antiviral agents, and antifungal agents.

The peptide of the invention can be administered parenterally by injection or by gradual infusion over time. The peptide can be administered intravenously, intraperitoneally, intramuscularly, subcutaneously, intracavity, or transdermally. Preferred methods for delivery of the peptide include orally, by encapsulation in microspheres or proteinoids, by aerosol delivery to the lungs, or transdermally by iontophoresis or transdermal electroporation. Other methods of administration will be known to those skilled in the art.

Preparations for parenteral administration of a peptide of the invention include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

The invention provides a method of treating or ameliorating an endotoxemia or septic shock (sepsis) associated disorder, or one or more of the symptoms of sepsis comprising administering to a subject displaying symptoms of sepsis or at risk for developing sepsis, a therapeutically effective amount of a cationic peptide of the invention, for example, SEQ ID NO:1 to SEQ ID NO:11 or analogs, derivatives, or conservative variations thereof. The term "ameliorate" refers to a decrease or lessening of the symptoms of the disorder being treated. Such symptoms which may be ameliorated include those associated with a transient increase in the blood level of TNF (tumor necrosis factor), such as fever, hypotension, neutropenia, leukopenia, thrombocytopenia, disseminated intravascular coagulation, adult respiratory distress syndrome, shock and multiple organ failure. Patients who require such treatment include those at risk for or those suffering from toxemia, such as endotoxemia resulting from a gram-negative bacterial infection, venom poisoning, or hepatic failure, for example. In addition, patients having a gram-positive bacterial, viral or fungal infection may display symptoms of sepsis and may benefit from such a therapeutic method as described herein. Those patients who are more particularly able to benefit from the method of the invention are those suffering from infection by *E. coli, Haemophilus influenza B, Neisseria meningitides, staphylococci,* or *pneumococci*. Patients at risk for sepsis include those suffering from gunshot wounds, renal or hepatic failure, trauma, burns, immunocompromised (HIV), hematopoietic neoplasias, multiple myeloma, Castleman's disease or cardiac myxoma.

The term "therapeutically effective amount" as used herein for treatment of endotoxemia refers to the amount of cationic peptide used is of sufficient quantity to decrease the subject's response to LPS and decrease the symptoms of sepsis. The term "therapeutically effective" therefore includes that the amount of cationic peptide sufficient to prevent, and preferably reduce by at least 50%, and more preferably sufficient to reduce by 90%, a clinically significant increase in the plasma level of TNF. The dosage ranges for the administration of cationic peptide are those large enough to produce the desired effect. Generally, the dosage will vary with the age, condition, sex, and extent of the infection with bacteria or other agent as described above, in the patient and can be determined by one skilled in the art. The dosage can be adjusted by the individual physician in the event of any contraindications. In any event, the effectiveness of treatment can be determined by monitoring the level of LPS and TNF in a patient. A decrease in serum LPS and TNF levels should correlate with recovery of the patient.

In addition, patients at risk for or exhibiting the symptoms of sepsis can be treated by the method as described above, further comprising administering, substantially simultaneously with the therapeutic administration of cationic peptide, an inhibitor of TNF, an antibiotic, or both. For example, intervention in the role of TNF in sepsis, either directly or indirectly, such as by use of an anti-TNF antibody and/or a TNF antagonist, can prevent or ameliorate the symptoms of sepsis. Particularly preferred is the use of an anti-TNF antibody as an active ingredient, such as a monoclonal antibody with TNF specificity as described by Tracey et al. (*Nature* 330:662, 1987).

A patient who exhibits the symptoms of sepsis may be treated with an antibiotic in addition to the treatment with cationic peptide. Typical antibiotics include an aminoglycoside, such as gentamicin or a beta-lactam such as penicillin, or cephalosporin or any of the antibiotics as previously listed above. Therefore, a preferred therapeutic method of the invention includes administering a therapeutically effective amount of cationic peptide substantially simultaneously with administration of a bactericidal amount of an antibiotic. Preferably, administration of cationic peptide occurs within about 48 hours and preferably within about 2–8 hours, and most preferably, substantially concurrently with administration of the antibiotic.

The term "bactericidal amount" as used herein refers to an amount sufficient to achieve a bacteria-killing blood concentration in the patient receiving the treatment. The bactericidal amount of antibiotic generally recognized as safe for administration to a human is well known in the art, and as is known in the art, varies with the specific antibiotic and the type of bacterial infection being treated.

Because of the antibiotic, antimicrobial, and antiviral properties of the peptides, they may also be used as preservatives or sterillants of materials susceptible to microbial or viral contamination. The peptides of the invention can be utilized as broad spectrum antimicrobial agents directed toward various specific applications. Such applications include use of the peptides as preservatives in processed foods (organisms including Salmonella, Yersinia, Shigella), either alone or in combination with antibacterial food additives such as lysozymes; as a topical agent (Pseudomonas, Streptococcus) and to kill odor producing microbes (Micrococci). The relative effectiveness of the cationic peptides of the invention for the applications described can be readily determined by one of skill in the art by determining the sensitivity of any organism to one of the peptides. The peptides of the invention are useful for inhibition of the growth of bacteria and fungi and inhibition of the replication of enveloped viruses including vesicular stomatitis virus, influenza A virus, human immunodeficiency virus (HIV)-1, herpes virus, hepatitis B and C viruses, and the like.

The following examples are intended to illustrate but not limit the invention. While they are typical of those that might be used, other procedures known to those skilled in the art may alternatively be used.

EXAMPLE 1

Mic Values for Cationic Peptides

Strains and Reagents

The bacterial strains used for antimicrobial activity assays included *E. coli* UB1005 (F$^-$, nalA37, metB1) and its outer membrane deficient mutant DC2 (16), *E. coli* KF130 (gyrA) (Hooper et al. (1987) *Am. J. Med.* 82:(Suppl. 4A),12–20), wild tppe strains of *S. typhimurium* 14028s (Fields et al. (1989) *Science* 243:1059–1062), *S. aureus* ATCC25923, *S. aureus* SAP0017 and R147. Also included was a clinical isolate of *S. epidermidis* were obtained from Dr. D. Speert, Department of Medicine, University of British Columbia, and *P. aeruginosa* PAO1 (Hancock and Carey (1979) *J. Bacteriol.* 140:902–910), H374 and H744 (Poole et al. (1993) *J. Bacterial.*175:7363–7372.) and *E. faecalis* ATCC 29212. Antifungal activity was tested using a clinical lab isolate of *Candida albicans*. All the strains were grown in Mueller Hinton (MH) broth (Difco Laboratories, Detroit, Mich.) at 37° C. unless otherwise indicated. The lipopolysaccharides (LPS) of *E. coli* UB1005 and *P. aeruginosa* H103 used for the dansyl-polymyxin B replacement assay were isolated as described by Moore et al. ((1986) *Antimicrobial. Agents Chemother.* 29:496–500). Polymyxin B, 1-N-phenylnapthylamine (NPN), carbonyl cyanide-m-chlorophenyl hydrazone (CCCP), Re LPS from *S.* Minnesota R595 (Re mutant) and LPS from *E. coli* 0111 :B4 were purchased from Sigma Chemicals Co. (St. Louis, Mo.). Dansyl polymyxin B was synthesized as described previously (Moore et al. (1986) *Antimicrobial. Agents Chemother.* 29:496–500). The lipids 1-pamitoyl-2-oleoyl-sn-glycero-3-phosphocholine (POPC), 1-palmitoyl-2-oleoyl-sn-glycero-3-phosphoglycerol (POPG), 1-palmitoyl-2-oleoyl-sn-glycero-3-phosphoethanolamine (POPE) and phosphatidylglycerol from egg yolk (egg-PG) were purchased from Avanti Polar Lipids Inc. (Alabaster, Ala.). The fluorescent dye 3,3-dipropylthiacarbocyanine (diSC$_3$5) was purchased from Molecular Probes (Eugene, Oreg.).

MIC Assay p The minimum inhibitory concentrations of (MIC) of several invention peptides were determined using methods described elsewhere (Wu and Hancock, (1999) *J. Biol Chem.* 274:29–35). Cells were grown overnight at 37EC in LB-S (Luria broth without any salt supplement) and diluted one in 10,000 in the same medium to give concentrations of about $10^4$ to $10^5$ CFU/ml. The broth dilutions were set up in a 96-well microtiter plate by putting 200 μl of LB-S containing the initial concentration of antibiotic or compound in column 1 and 100 Φl of the same medium in columns 2–12. The compounds were diluted by taking 100 μl of broth from column 1 and mixing it with column 2, resulting in a one in two dilution. This procedure was continued to column 10. Finally, 10 μl of bacteria were pipetted into columns 1–11, and the plates incubated overnight at 37° C. The next day the plates were scored for growth in the wells, and the MIC determined.

Hemolytic Assay

Hemolytic activity of invention peptides was tested against human red blood cells. Freshly collected human blood treated with heparin was centrifuged to remove the buffy coat, and the erythrocytes thereby obtained were washed three times in saline (0.85% NaCl). Serial dilutions of the peptides in saline were prepared in round-bottomed microtiter plates using total volumes of 100 μl. Red blood cells were diluted with saline to 1/25 of a packed cell volume, and 50 μl of cells were added to each well. Plates, while rocking, were incubated at 37° C., and the concentration of the peptide required for lysis after 4 h was taken as the minimal hemolytic concentration.

TABLE 1

| | MIC (µg/ml) | | | |
| | | SEQ ID NO: | | |
| Cells | PMI* | 11 | 4 | 3 |
|---|---|---|---|---|
| Escherichia coli UB1005 | 0.125 | 0.25 | 0.25 | 0.25 |
| E. coli DC2 | 0.125 | 0.25 | 0.125 | 0.25 |
| E. coli KF130 | 0.125 | 0.25 | 0.125 | 0.25 |
| Salmonella typhimurium 14028s | 0.25 | 0.5 | 0.5 | 0.5 |
| Pseudomonas aeruginosa PAO1 | 0.25 | 1 | 1 | 2 |
| P. aeruginosa H374 | 0.25 | 0.5 | 0.5 | 2 |
| P. aeruginosa H744 | 0.25 | 1 | 1 | 2 |
| Staphylococcus aureus ATCC 25923 | 0.5 | 1 | 1 | 1 |
| S. aureus R147 | 0.5 | 1 | 1 | 1 |
| S. aureus SAP0017 | 0.5 | 1 | 1 | 1 |
| Staphylococcus epidermidis | 0.25 | 0.25 | 0.5 | 0.5 |
| Enterococcus facaelis | 0.25 | 0.5 | 0.25 | 0.5 |
| Candida albicans | 1 | 2 | 4 | 16 |
| Human Red Blood Cells | 21.3 | 42.6 | 85 | 85 |

*PMI = Polyphemusin I.

The results summarized in Table 1 show that the tested peptides (SEQ ID NO's: 3, 4, and 11) are effective antimicrobial agents at concentrations ranging from 0.125 to 0.5 µg/mL for a variety of gram positive and gram negative bacteria. In addition, all peptides were effective against the yeast *Candida albicans*. Modification of the peptides, such as methyl ester modification, or L to D amino acids, provides a broader class of active antimicrobial agents.

Polyphemusin I and tested peptides (SEQ ID NO's:3, 4, and 11) show hemolytic activity in a hemolytic assay using red blood cells.

EXAMPLE 2

Cationic Peptide Reduction of LPS-Induced TNF

The ability of invention peptides to reduce LPS-induced tumor necrosis factor (TNF) production was tested in an in vitro assay. The murine macrophage cell line RAW 264.7 was obtained from American Type Culture Collection (Manassas, Va.) and grown in DMEM medium supplemented with 10% fetal calf serum. The cells were plated at a density of 106 cells/well in 24 well plates, incubated overnight, then washed with fresh medium. *E. coli* 0111 :B4 (100 ng/ml) was added at time 0 to RAW macrophages. Invention peptides 20 µg/m were added at time 0, 30 and 60 minutes and the cells were stimulated for 6 hours. Levels of TNF and interleukin-6 (IL-6) were measured after 6 hours. The cell supernatants were assayed for TNF-α and IL-6 by enzyme-linked immunosorbent assays (ELISA) (Endogen, Hornby, ON, Canada), following the manufacturer's suggestions. The results are shown in Table 2

TABLE 2

| Peptide Treatment (20 µg/ml) | Inhibition of TNF-α (%) | Inhibition of IL-6 (%) |
|---|---|---|
| Polyphemusin I | 83 ± 6 | 84 ± 3 |
| SEQ ID NO:11 (PV5) | 90 ± 6 | 91 ± 4 |
| SEQ ID NO:4 (PV7) | 61 ± 5 | 77 ± 6 |
| SEQ ID NO:3 (PV8) | 55 ± 5 | 70 ± 6 |

Invention peptides are able to inhibit *E. coli* 0111 :B4 LPS induced production of TNF-α and IL-6 in RAW macrophages. The peptides, at 20 µg/ml, were all able to significantly inhibit cytokine production by LPS-stimulated macrophages (Table 2). SEQ ID NO:11 (PV5) was the best inhibitor of TNF-α and IL-6.

EXAMPLE 3

Protection from Lethal LPS Endotoxicity in a Mouse Endotoxic Shock Model

Invention peptides were assayed for their ability to protect against *P. aeruginosa* infection in a neutropenic mouse mode. Female CD-1 mice, made neutropenic by three injections of cyclophosphamide (see Gough et al., (1996) *Infect. Immun.* 64:4922–4927) were injected intraperitoneally with a 100% lethal dose of *P. aeruginosa* M2 (approximately 200 organisms). Thirty minutes later, mice were injected intraperitoneally with invention peptides (200 µg/100 µl) Survival was assessed 24 to 72 hours later.

The ability of invention peptides to protect against LPS-induced endotoxemia was assessed in vivo. Mice (8–10 weeks old) were injected intraperitoneally with 20 µg D-galactosamine (Dgal) to sensitize them to LPS according to the method of Galanos (Galanos et al. (1979) *Proc. Natl. Acad. Sci., USA*, 76:5939–5943). Endotoxic shock was induces by intraperitoneal injections of 3 µg/mL *E. coli* 111 :B4 LPS in phosphate-buffered saline (PBS). Invention peptides (200 µg/100 µl sterile water) were injected intraperitoneally at a separate site within 10 min of LPS injection, and survival was monitored up to 24 h following injection.

The results of these studies are shown in Table 3.

TABLE 3

| | P. aeruginosa infection[a] | | LPS-Endotoxemia[b] |
|---|---|---|---|
| Treatment | Mean Time to Death (h) | Survival (%) | Survival (%) |
| Control (no peptide) | 24 | 0 | 0 |
| Polyphemusin I | 52 | 20 | 10 |
| SEQ ID NO:11 (PV5) | 57 | 40 | 50 |
| SEQ ID NO:4 (PV7) | 61 | 40 | 40 |
| SEQ ID NO:3 (PV8) | >72 | 60 | 20 |

[a]Groups of 5 mice.
[b]Groups of 10 mice.

Table 3 illustrates that invention peptides are able to provide protection against *P. aeruginosa* infection, and that this protection is superior to the parent peptide, i.e., polyphemusin I. More than 50% of the mice treated with invention peptides survive greater than 48 hours. In contrast, mice that received no peptides died rapidly after bacterial challenge, showing 50% mortality within 24 hours and 100% mortality within 41 hours. Mice not challenged with bacterial infection showed 100% survival during the observation period.

Table 3 further illustrates that invention peptides are able to provide protection against endoxemia. Bacterial endotoxin (LPS) is highly toxic and can cause high mortality in both humans and animals when released during a Gram-negative bacterial infection. Galactosamine-treated mice given moderate doses of endotoxin usually die form endotoxic shock within 17 hours. Invention peptides are able to provide protection from endotoxic-induced death.

EXAMPLE 4

Peptide Binding Affinity for LPS

To determine whether invention peptides are able to interact with the LPS of Gram-negative bacterial outer membrane, the binding affinity of peptide for LPS was determined using a dansyl polymyxin B displacement assay (Moore et al. (1986) *Antimicrobial Agents Chemother.* 29:496–500). The assay uses dansyl polymyxin, a cationic probe that is highly fluorescent only when bound and LPS isolated from *E. coli.* UB1005. The fraction of dansyl polymyxin B remaining bound to LPS is plotted as a function of peptide concentration, and from this data the concentration of peptide required to reduce the amount of bound dansyl polymyxin B (10 μM) by 50% of the maximal displacement ($I_{50}$) (Table 4). Maximal displacement of LPS was expressed as a percentage where 100% displacement of dansyl polymyxin B was taken as that observed with polymyxin B.

TABLE 4

| Peptide | $I_{50}$ (μM) | $I_{max}$ (%) | $P_{50}$ (μg/ml) |
|---|---|---|---|
| Polyphemusin I | 4.8 | 85 | 2.8 |
| SEQ ID NO:11 (PV5) | 3.0 | 87 | 3.7 |
| SEQ ID NO:4 (PV7) | 5.7 | 76 | 4.1 |
| SEQ ID NO:3 (PV8) | 4.9 | 93 | 3.9 |
| Polymyxin B | 5.6 | 100 | ND |

The results in Table 4 show that all peptides tested are able to displace dansyl polymyxin to a similar extent with $I_{50}$ values that differ by less than two-fold.

EXAMPLE 5

Membrane Permeabliization Activity

The outer membrane permeabilization activity of invention peptides was determined by the 1-N-phenylnapthylamine (NPN) uptake assay of Loh et al. ((1984) *Antimicor. Agents Chemother.* 26:546–551), using intact cells of *E. coli* UB1005.

The cytoplasmic membrane depolarization activity of the peptides was determined (Wu and Hancock (1999) *J. Biol. Chem.* 274:29–35) using the membrane potential sensitive dye 3,3-dipropylthiacarbocyanine $diSC_35$ (28) and *E. coli* DC2. Bacterial cells in mid-log phase were centrifuged, washed in 5 mM HEPES, pH 7.8, and resuspended in the same buffer to an $OD_{600}$ of 0.05. A stock solution of $diSC_35$ was added to a final concentration of 0.4 μM and quenching was allowed to occur at room temperature for 20–30 min. Then KCl was added to the cell suspension to a final concentration of 100 mM to equilibrate the cytoplasmic and external $K^+$ concentrations. A 2-mL cell suspension was placed in a 1 cm cuvette and the desired concentration of tested peptide was added. Changes in fluorescence due to the disruption of the membrane potential in the cytoplasmic membrane were continuously recorded using a Perkin-Elmer model 650-10S spectrofluorimeter at an excitation wavelength of 622 nm and an emission wavelength of 670 nm. The concentration of peptide leading to a 50% of maximal increase in NPN uptake was recorded as the $P_{50}$.

The ability of the peptides to permeabilize the outer membrane of *E. coli* UB1005 is shown in Table 4. NPN is a small hydrophobic molecule that is normally excluded by the intact outer membrane but exhibits increased fluorescence when it partitions into the bacterial outer membrane after disruption of outer membrane integrity. Therefore, an increase in fluorescence in the presence of a peptide indicates the ability of peptide to permeabilize the bacterial outer membrane. As shown in Table 4, both polyphemusin I and invention peptides were able to mediate NPN uptake across the outer membrane to similar extents and the $P_{50}$ values varied less than 30% from a mean of 3.6 μg/ml.

After passage through the outer membranes of Gram-negative bacteria, or through the permeable cell walls of Gram-positive bacteria, cationic antimicrobial peptides interact with the bacterial cytoplasmic membrane. The ability of each peptide to depolarize the *E. coli* cytoplasmic membrane potential gradient is shown in FIG. 3. Polyphemusin I is a relatively good membrane permeabilizer and causing rapid dissipation of the cytoplasmic membrane potential within 5 min at a concentration of 0.25 μg/ml (2×MIC) as indicated by the release of the membrane potential sensitive fluorescent dye $diSC_35$ from cells upon addition of peptide to the cell suspension (FIG. 3). In contrast, at the same peptide concentration, both SEQ ID NO: 4 (PV7) and SEQ ID NO:3 (PV8) caused significantly slower membrane permeabilization, with a lag time of more than 3 min before any fluorescence increase was detected (FIG. 3), and a maximum dye release that was less than 50% that mediated by polyphemusin I. At 0.25 μg/ml (1×MIC), SEQ ID NO:11 (PV5) was unable to cause a significant level of dye release from cells.

EXAMPLE 6

Peptide Interactions With Liposomes

To understand the interaction of peptides with the bacterial cytoplasmic membrane, model systems were used. The tryptophan residue at position 3 of invention peptides provided the opportunity to monitor binding to liposomes since the fluorescence emission of this amino acid is sensitive to its environment. Unilamellar liposomes (0.1 μm) in HEPES buffer, pH7.5, were prepared with POPC/POPG (7:3 w/w) or POPC only, using the freeze-thaw method (see Mayer et al. (1985) *Biochim. Biophys.* Acta 817:193–196) followed by extrusion through 0.1 μm double stacked Nuclepore filters using an extruder device (Lipex Biomembranes, Vancouver, BC. Canada). The tryptophan fluorescence and KI quenching measurements were performed using a Luminescence Spectrometer, LS50B (Perkin Elmer) (see Eftink and Ghiron (1976) *J. Phys. Chem.* 80:486–493).

TABLE 5

| | | SEQ ID NO: | |
| PEPTIDE | PMI | 11 | 4 | 3 |
|---|---|---|---|---|
| $E_{max}$ (nm) (HEPES) | 356 | 356 | 354 | 353 |
| $E_{max}$ (nm) (POPC/ POPG) | 342 | 342 | 343 | 338 |
| Intensity change (fold) | 1.3 | 3.7 | 2.4 | 1.9 |
| Accessibility to quencher $KI^b$ | – | – | – | – |
| $E_{max}$ in POPC (nm) | 353 | 354 | 353 | 350 |
| Intensity change (fold) | –0.5 | 0.7 | 1.5 | –0.7 |
| Accessibility to quencher $KI^b$ | + | + | + | + |

PMI = Polyphemusin I.
[b]–, the fluorescence of tryptophan residue could not be quenched by the aqueous quencher KI; +, the fluorescence of tryptophan residue was suppressed by the aqueous quencher KI in a concentration dependent manner.

Upon addition of each peptide to anionic liposomes with a composition that reflected the uncharged to charged phospholipid ratio of the *E. coli* cytoplasmic membrane (POPC:POPG, 7:3), the fluorescence emission maxima exhibited a blue shift of 11 to 14 nm and marked increase in fluorescence emission intensity (1.3–3.7 fold), indicating a relocation of this tryptophan residue into a more hydrophobic environment (Table 5). No significant differences were observed among these peptides.

Figure 4:
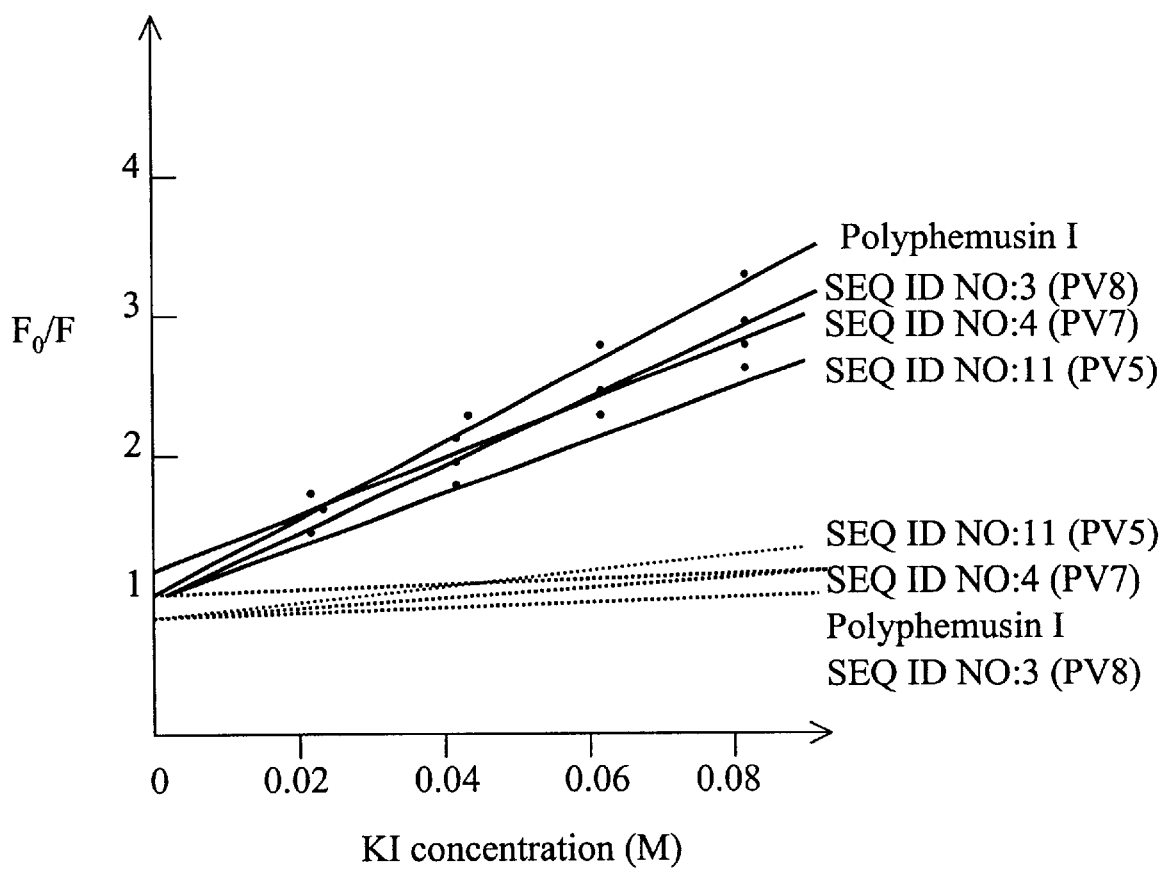
FIG. 4 is a Stern-Volmer plot of the quenching of peptide tryptophan fluorescence data by an aqueous quencher KI. Dotted lines represent data for peptides added to a suspension of liposomes (POPC/POPG, 7:3), while solid lines represent data for quenching in 10 mM HEPES buffer, pH7.5.

To confirm these data, the ability of the water-soluble quencher KI to suppress peptide tryptophan fluorescence was examined. In buffer, the water-soluble quencher KI was able to completely suppress fluorescence in a concentration-dependent manner (FIG. 4). However, when the quencher was added to peptide in the context of liposomes (POPC/POPG, 7:3), no decrease in fluorescence intensity was observed, indicating that the tryptophan residue of the peptides in liposomes was inaccessible to this aqueous quencher (FIG. 4). The addition of peptide to uncharged POPC liposomes did not result in a significant blue shift (generally less than 2 nm), and the tryptophan fluorescence of three of the peptides decreased, whereas that of SEQ ID NO:4 (PV7) increased only about 50% in POPC liposomes compared to HEPES buffer (Table 5). Addition of the quencher KI to peptide in the context of POPC liposomes resulted in suppression of tryptophan fluorescence in a concentration dependent manner similar to peptide in buffer (Table 5), suggesting that the tryptophan residue of the polyphemusin peptides in POPC was still accessible to the quencher. Thus the changes in intensity of tryptophan fluorescence in the presence of POPC probably reflected light scattering by the liposomes and I or association of the peptides with the surfaces of liposomes.

Langmuir Monolayer Assay

Lipid monolayers were formed by applying the appropriate lipids dissolved in hexane or chloroform onto water contained in a circular Teflon trough (d=4.5 cm, total volume of 11.5 ml). A small port in the side of the trough enabled injection of reagents into the subphase without disruption of the monolayer. The subphase was gently mixed with a magnetic stir bar at 45 rpm. Surface pressure measurements were obtained by using the Whilhelmy plate method (Mayer et al. (1983) *Biochemistry* 22:316–321). The plate was cleaned with methanol three times and thoroughly rinsed with double-distilled water prior to each surface pressure measurement. The experiments were run at 23° C.

An LPS monolayer film on the air-water interface was obtained by spreading the LPS solution (0.5 mg/ml in chloroform/methanol/$H_2O$, 17/7/1, v/v) (Fried and Rothfield. (1978) *Biochim. Biophys.* Acta 514:69–82) onto buffer alone (5 mM HEPES and 150 mM NaCl) or in the presence of either 2 mM or 5 mM $MgCl_2$.

Figure 5A:
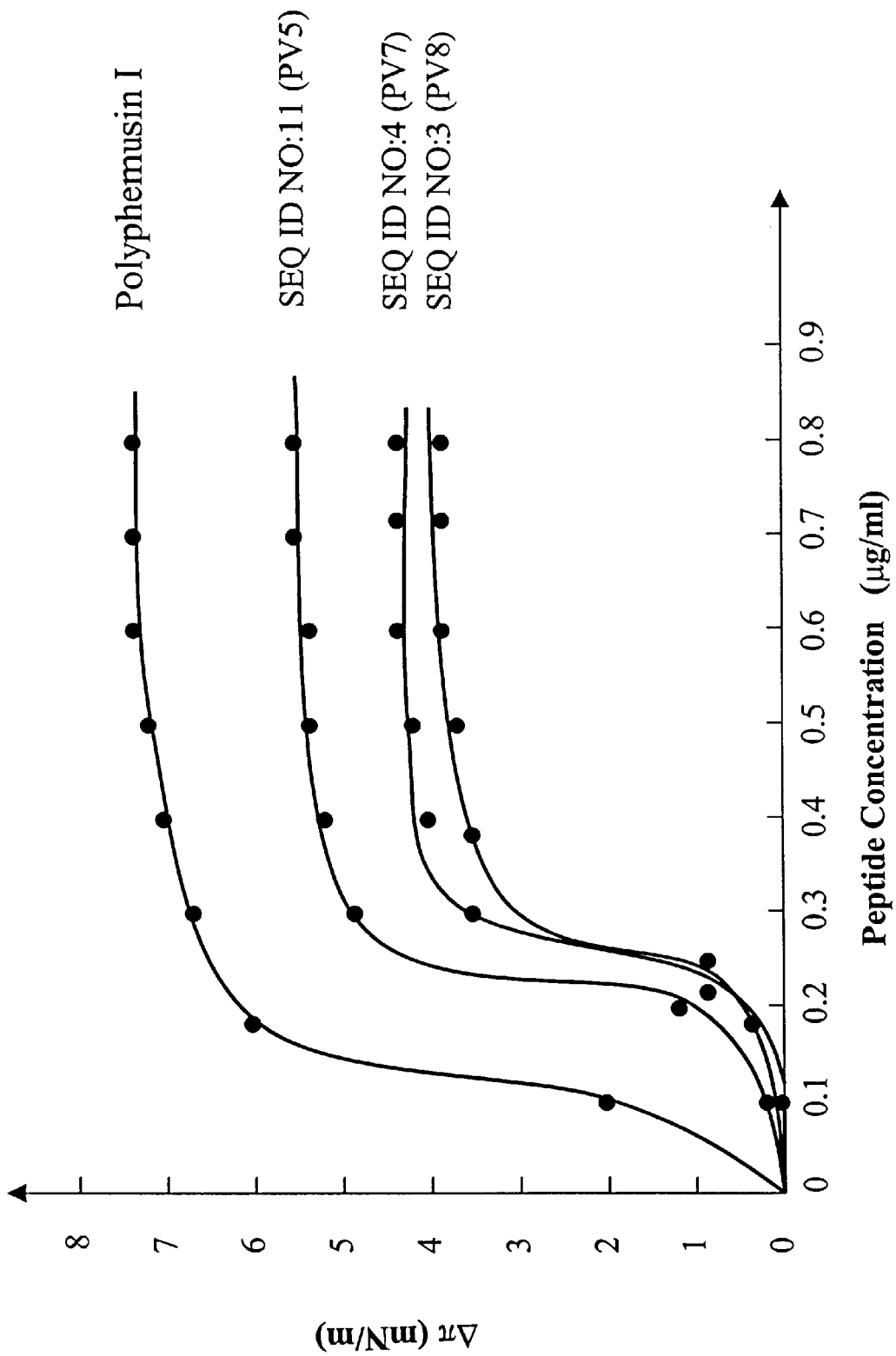
FIGS. 5A through 5B shows the influence of peptide addition to the aqueous subphase bathing lipid monolayers on surface pressure, as measured in a Langmuir balance.

The phospholipids of *E. coli* cells comprise a mixture of the neutral lipid phosphatidyl ethanolamine (PE), and the anionic lipids phosphatidyl glycerol (PG) and cardiolipin (CL), in the ratio of 78:4.7:14.4, in addition to some minor lipid species (Hristova et al. (1997) *J. Biol. Chem.* 272:24224–24233). Monolayers were made from POPE:egg-PG:CL (78:4.7:14.4) to mimic the *E. coli* cytoplasmic membrane, and the ability of polyphemusin-like peptides to interact with such monolayer was assessed. Molecules which interacts only with the headgroups of a given lipid monolayer should not increase the surface pressure of the monolayer. Thus when a protein or peptide molecule is injected into the subphase bathing a monolayer, a corresponding surface pressure change ($\Delta\pi$) can be interpreted as resulting from the protein or peptide inserting into and disturbing the fatty acyl core of the membrane. FIG. 5A shows the variation in surface pressure as a function of peptide concentration. All peptides appeared to induce increases in surface pressure as a sigmoidal function of peptide concentration (FIG. 5A), a result consistent with a cooperative interaction of the peptide molecules with a monolayer. Polyphemusin I was the most effective peptide at modulating the surface pressure as indicated by the plateau $\Delta\pi$ which were 7.4, 5.2, 4.7 and 4.5 mN/m for polyphemusin I, SEQ ID NO:11 (PV5), SEQ ID NO:4 (PV7) and SEQ ID NO:3 (PV8), respectively.

Figure 5B:
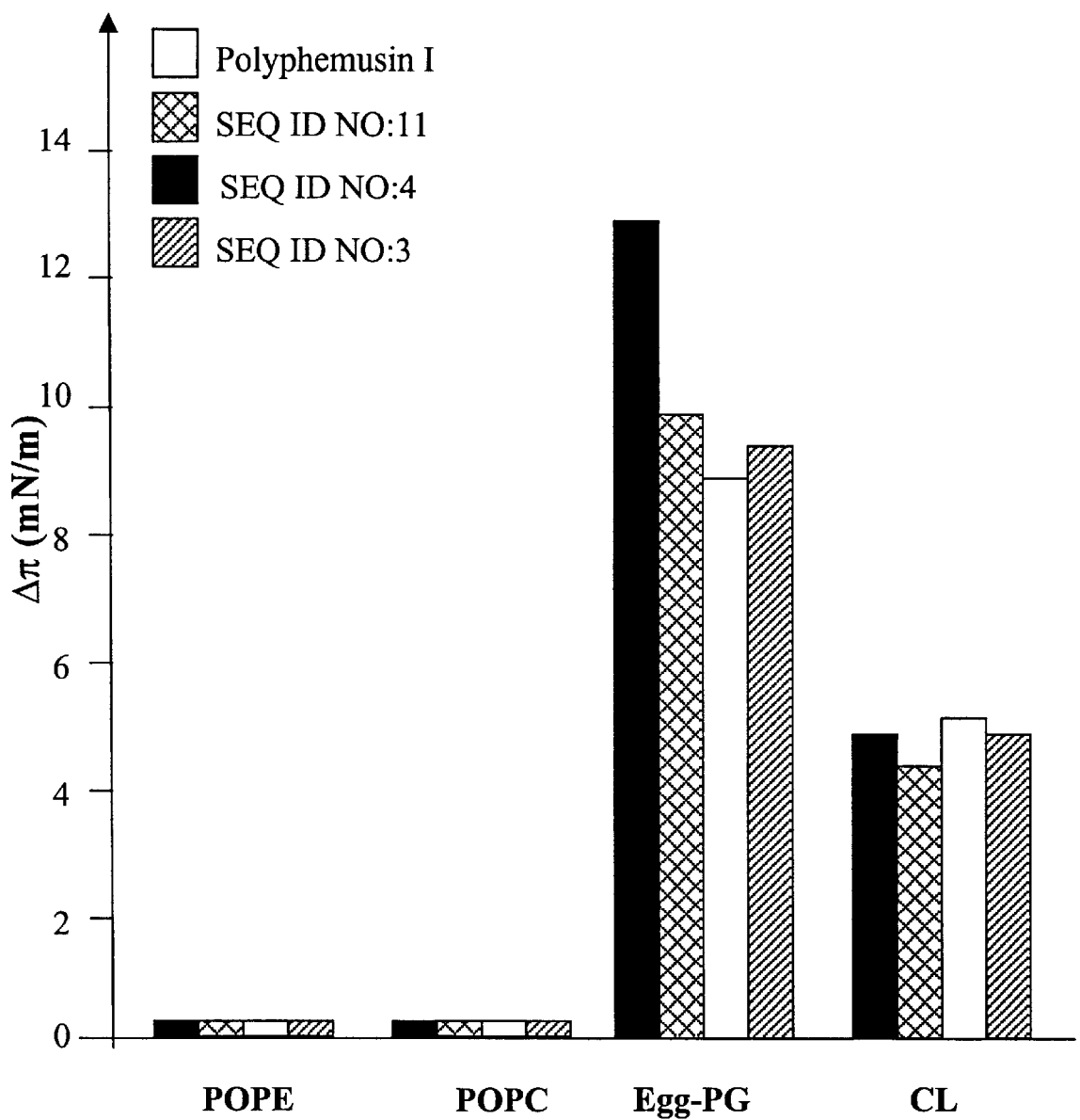

The lipid specificity of each peptide was monitored by assessing the extent of the surface pressure change upon addition of 1 $\mu$g/ml of peptide to the subphase of monolayers of POPC, POPE, egg-PG or CL (FIG. 5B). All peptides selectively interacted with negatively charged lipids and generally had a greater effect on PG than on CL monolayers. Consistent with the observations in FIG. 5A, polyphemusin I demonstrated the largest effect on PG monolayers. However none of the peptides were able to penetrate monolayers made with neutral lipids such as POPC or POPE.

Figure 6:
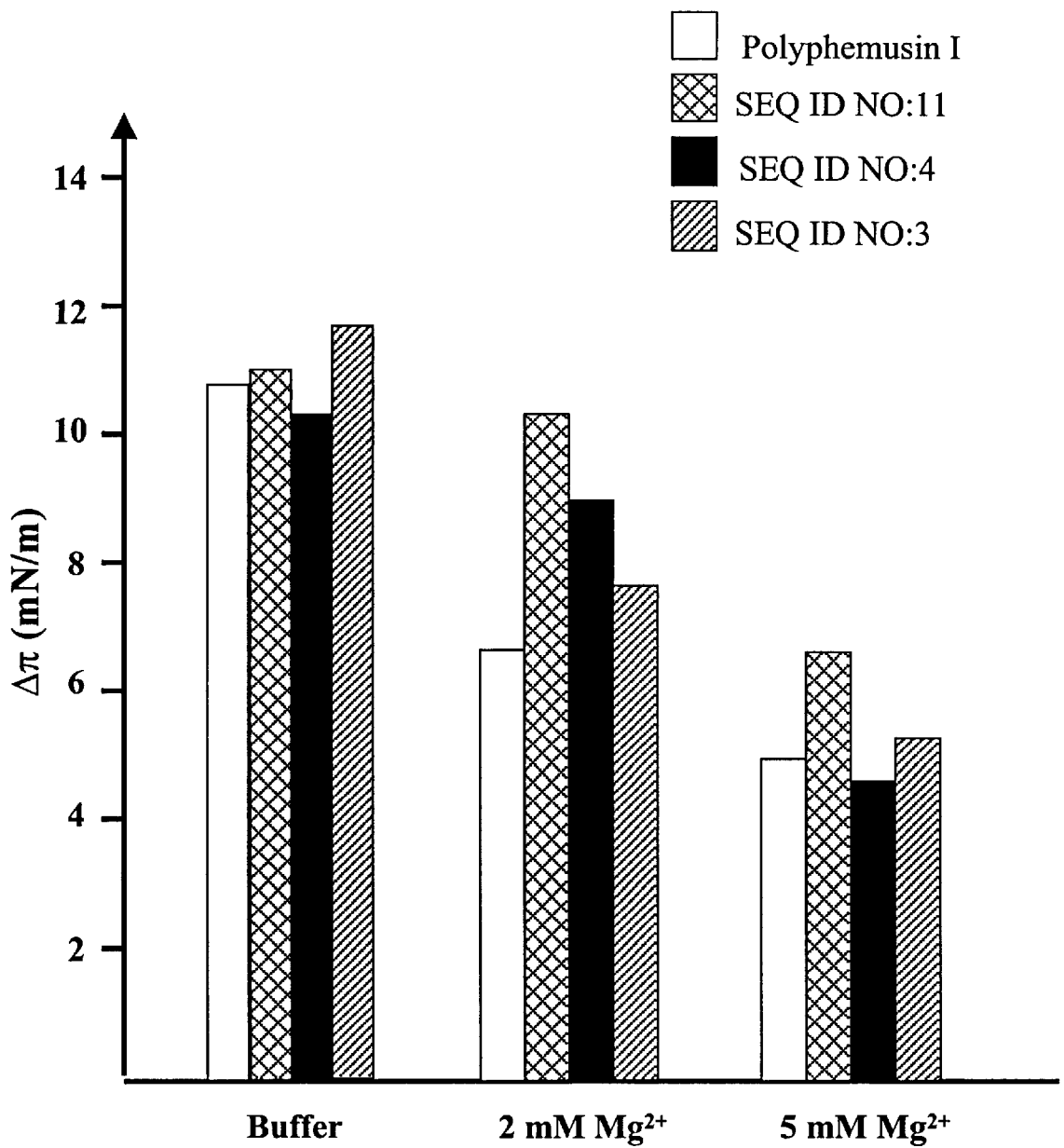
FIG. 6 shows the influence on surface pressure of the addition of 0.8 µg/ml peptide to the aqueous subphase bathing Salmonella minnesota Re LPS monolayers. The $Mg_{2+}$ concentration of the subphase was varied. The monolayer was spread achieving an initial pressure of 18±1 mN/m and allowed to stabilize for 5 min before addition of peptide.

To mimic interactions with the outer membrane, monolayers made with LPS were employed to mimic the outer leaflet of Gram-negative bacterial outer membrane. Thus the ability of a peptide to interact with an LPS monolayer should reflect its ability to penetrate the outer membrane. As shown in FIG. 6, generally no substantial difference was observed between polyphemusin I and its variants in terms of their ability to interact with LPS monolayers. These peptides demonstrated similar ability to penetrate LPS monolayer in the absence of added $Mg^{2+}$. Consistent with the observation that peptides generally interact with divalent cation binding sites on LPS, the addition of $Mg^{2+}$ resulted in a concentration dependent, moderate reduction in peptide-mediated surface pressure change (FIG. 6).

EXAMPLE 7

Characterization of Polyphemusin-Like Peptides

Circular Dichroism (CD) Spectrometry

CD spectra of invention peptides were recorded on a Model J-810 spectropolarimeter (Jasco, Tokyo, Japan) connected to a Jasco spectra manager, using a quartz cell of 1-mm path length. CD spectra were measured at 25° C., between 190 and 250 nm at a scanning speed of 10 $\mu$m/min in 10 mM sodium phosphate buffer, pH7.2 in the presence or absence of 10 mM SDS. Minor contributions of circular differential scattering by buffer or SDS were eliminated by subtracting the CD spectrum of buffer or SDS alone from that of peptide in buffer or in SDS. The spectra shown are the averages of ten scans.

Circular dichroism (CD) spectroscopy was carried out for certain invention peptides. The CD spectrum of polyphemusin I in buffer displayed two positive bands at about 224 nm and 202 nm, a spectrum typical of a structure dominated by a type II $\beta$-turn (FIG. 2), and virtually identical to the published CD spectrum for tachyplesin I (Rao (1999) *Arch. Biochem. Biophys.* 361:127–134). It is worthwhile to note that aromatic amino acids have been suggested to partially contribute to the 224 nm band (Chang et al. (1978) *Anal. Biochem.* 91:13–17). An anionic-membrane environment was mimicked using 10 mM SDS. Under this conditions, polyphemusin I exhibits a different CD spectrum with a strong positive ellipticity near 200 nm and a negative ellipticity near 217 nm (FIG. 2A), both of which are typical of $\beta$-sheet structures and were also observed for tachyplesin I in the presence of acidic liposomes (Mayer et al. (1983) *Biochemistry* 22:316–321). Therefore although the NMR structure of polyphemusin I was not determined, it is very likely to be similar to that of tachyplesin I with an antiparallel $\beta$-sheet structure stabilized by disulphide bridges and a type II $\beta$-turn. The three peptides examined (SEQ ID NO's:3, 4, and 11) had similar spectra both in the presence of 10 mM SDS and in phosphate buffer, although the magnitude of the peak ellipticities varied from peptide to peptide and especially the positive peak at around 200–204 nm in the presence of phosphate buffer varied somewhat in magnitude and actual peak wavelength. Possibly, these peptides displayed a less pronounced $\beta$-turn in phosphate buffer due to the residue changes induced in this region, although similar $\beta$-sheet structure was evident in SDS.

Although the invention has been described with reference to the presently preferred embodiment, it should be understood that various modifications can be made without departing from the spirit of the invention. Accordingly, the invention is limited only by the following claims.

What is claimed is:

1. An isolated peptide having antimicrobial activity and an amino acid sequence selected from the group consisting of:

WCFZ$_5$VCZ$_2$RGZ$_3$CRZ$_2$KCRR (SEQ ID NO:14),
Z$_2$RWCFRVCYZ$_3$GZ$_2$CZ$_3$Z$_5$Z$_2$CR (SEQ ID NO:15),
RRWCFZ$_5$VCZ$_3$RGZ$_4$CYZ$_4$Z$_4$CRZ$_1$ (SEQ ID NO:16),
RZ$_5$WCZ$_3$Z$_2$Z$_3$CYRGFCZ$_3$Z$_2$Z$_5$CR (SEQ ID NO:17),
RRWCZ$_3$RVCYZ$_5$GFCYRKCR (SEQ ID NO:18), and
RRWCFRVCYRGZ$_3$FCYRKCR (SEQ ID NO:19);

wherein $Z_1$ is an amino acid residue having a basic side chain or absent, $Z_2$ is an amino acid residue having a basic or aromatic side chain, $Z_3$ is an amino acid residue having a basic side chain, $Z_4$ is arginine, valine or alanine, and $Z_5$ is an amino acid residue having an aromatic or aliphatic side chain.

2. The peptide of claim 1, wherein:

$Z_1$ is lysine, arginine, histidine, or is absent;
$Z_2$ is lysine, arginine, histidine, phenylalanine, tyrosine or tryptophan;
$Z_3$ is lysine, arginine or histidine;
$Z_4$ is arginine, valine or alanine; and
$Z_5$ is alanine, valine, isoleucine, leucine tyrosine, phenylalanine, or tryptophan.

3. The peptide of claim 1, wherein the peptide has an amino acid sequence selected from a the group consisting of:

WCFAVCRRGRCRYKCRR (SEQ ID NO:1),
WCFAVCYRGRCRRKCRR (SEQ ID NO:2),
FRWCFRVCYKGRCRYKCR (SEQ ID NO:3),
RRWCFRVCYKGFCRYKCR (SEQ ID NO:4),
RRWCFRVCYRGFCRYFCR (SEQ ID NO:5),
RRWCFIVCRRGACYRRCR (SEQ ID NO:6),
RRWCFIVCRRGRCYVACRR (SEQ ID NO:7),
RVWCRRRCYRGFCRYFCR (SEQ ID NO:8),
RVWCRYRCYRGFCRRFCR (SEQ ID NO:9),
RRWCRRVCYAGFCYRKCR (SEQ ID NO: 10), and
RRWCFRVCYRGRFCYRKCR (SEQ ID NO:11).

4. The peptide of claim 1, wherein the peptide contains a carboxyl-terminal amide or ester.

5. The peptide of claim 4, wherein the carboxyl-terminal is an amide.

* * * * *